(12) United States Patent
Littlewood et al.

(10) Patent No.: US 8,428,735 B2
(45) Date of Patent: Apr. 23, 2013

(54) ELECTROTHERAPY APPARATUS

(75) Inventors: Roger Kenneth Littlewood, Axbridge Somerset (GB); Alexander John Ranald Macdonald, Bristol Avon (GB); Timothy William Coates, Winscombe Somerset (GB); Ivor Stephen Gillbe, Bristol Avon (GB)

(73) Assignee: Bioinduction Limited (GB)

( * ) Notice: Subject to any disclaimer, the term of this patent is extended or adjusted under 35 U.S.C. 154(b) by 33 days.

(21) Appl. No.: 13/197,452

(22) Filed: Aug. 3, 2011

(65) Prior Publication Data
US 2012/0022612 A1 Jan. 26, 2012

Related U.S. Application Data

(62) Division of application No. 11/569,366, filed as application No. PCT/GB2005/002075 on May 24, 2005, now abandoned.

(30) Foreign Application Priority Data

May 24, 2004 (GB) .................................... 0411610

(51) Int. Cl.
A61N 1/02 (2006.01)
(52) U.S. Cl.
USPC .......................................................... 607/46
(58) Field of Classification Search ...................... 607/46
See application file for complete search history.

(56) References Cited

U.S. PATENT DOCUMENTS

| | | | |
|---|---|---|---|
| 2,622,601 A | 12/1952 | Nemee | |
| 3,096,768 A | 7/1963 | Whitfield, Jr. | |
| 3,835,833 A | 9/1974 | Limoge et al. | |
| 3,908,669 A | 9/1975 | Man et al. | |
| 4,121,594 A | 10/1978 | Miller et al. | |
| 4,233,986 A | 11/1980 | Tannenbaum et al. | |
| 4,763,656 A | 8/1988 | Nauman | |
| 4,970,154 A | 11/1990 | Chang | |
| 4,989,605 A | 2/1991 | Rossen | |
| 5,052,391 A | 10/1991 | Silberstone et al. | |
| 5,512,057 A | 4/1996 | Reiss et al. | |
| 5,514,165 A * | 5/1996 | Malaugh et al. | 607/46 |
| 5,776,170 A | 7/1998 | MacDonald et al. | |
| 5,983,141 A | 11/1999 | Sluijter et al. | |
| 6,023,642 A | 2/2000 | Shealy et al. | |

(Continued)

FOREIGN PATENT DOCUMENTS

| GB | 2129243 | 5/1984 |
|---|---|---|
| GB | 2290033 | 12/1995 |

(Continued)

OTHER PUBLICATIONS

Abdalla E. et al., Information transport by sine-Gordon solitons in microtubules ArXiv:physics/0103042v115 Mar. 2001.

(Continued)

*Primary Examiner* — Eric D. Bertram
(74) *Attorney, Agent, or Firm* — McGarry Bair PC

(57) ABSTRACT

An apparatus for producing analgesia in a patient through electrical signals applied through electrodes to a patient's body, and methods of treating patients using the apparatus. The apparatus comprises a signal generator arranged to generate a biphasic waveform comprising successive cycles each containing a positive and negative pulse.

26 Claims, 7 Drawing Sheets

U.S. PATENT DOCUMENTS

| | | | |
|---|---|---|---|
| 6,161,044 A | 12/2000 | Silverstone | |
| 6,233,488 B1 | 5/2001 | Hess | |
| 6,246,912 B1 | 6/2001 | Sluijter et al. | |
| 6,711,442 B1 * | 3/2004 | Swerdlow et al. | 607/63 |
| 2002/0099412 A1 | 7/2002 | Fischell et al. | |
| 2003/0195581 A1 | 10/2003 | Meadows et al. | |
| 2003/0236558 A1 | 12/2003 | Whitehurst et al. | |
| 2004/0049240 A1 | 3/2004 | Gerber et al. | |

FOREIGN PATENT DOCUMENTS

| | | |
|---|---|---|
| JP | 8-500988 | 2/1996 |
| JP | 2004113485 A | 4/2004 |
| WO | 94/17855 | 8/1994 |
| WO | 03/066154 | 8/2003 |
| WO | 2004/007018 | 1/2004 |

OTHER PUBLICATIONS

Barnes et al., Modulation of neurogenic inflammation: novel approaches to inflammatory disease. Trends in Pharmacological Sciences 11:185-189.

Basbaum AI, Jessel TM (200) The perception of pain. In: Principles of Neural Science (Eds) Kandel ER, Schwartz JH, Jessel TM. Mcgraw-Hill. pp. 477-478.

Blake AD, Bot G, Reisine T (1997) Molecular Pharmacology of the cloned opioid receptors. In: (Ed) Borsook D. Molecular Neurobiology of Pain. Progress in Pain Research and Management., vel 9, IASP Press, Seattle, pp. 259-273.

Cahana A, Vutskits L. Muller D (2003) Acute differential modulation of synaptic transmission and cell survival during exposure to pulsed and continuous radiofrequency energy. The Journal of Pain 4:197-202.

Chen L, GuY, Huang L-Y (1995) The Mechanism of Action for the Block of NMDA Receptor Channels by the Opioid Peptide Dynorphin. the Journal of Neuroscience 15: 4602-4611.

Chung JM, Lee KH, Hori Y, Endo K, Willis WD (1984) Factors Influencing Peripheral Nerve Stimulation Produced D Inhibition of Primate Spinothalamic Tract Cells, Pain 19 (1984) 277-293.

Couthino V, Knopfel T (200) Metabotrophic Glutamate Receptors: Electrical and Chemical Signalling Properties. Neuroscientist 8(6):551-562.

Ferreira SH (1983) Prostaglandins: Peripheral and Central Analgesia. In: Advances in Pain Research and Therapy. vol. 5 (Eds) Bonica JJ et al. Raven Press. pp. 627-634.

Higuchi Y, Nashold BS, Sluitjer M. Cosman E, Pearlstein RD (200) Exposure of the Dorsal Root Ganglion in Rats to Pulsed Radiofrequency Currents Activates Dorsal Horn Lamina I and II Neurons. Neurosurgery 50:850-856.

Holsheimer J, Wessenlink WA (1997) Effect of anode-cathode configuration on paraesthesia in spinal cord stimulation. Neurosurgery 41:654-660.

Jansco N. Jansco-Gabor A, Szolcsanyi J (1967) Direct Evidence for Neurogenic Inflammation and its Prevention by Denervation and by Pre-Treatment with Capsaicin. Br J_Pharmac Chemother 31: 138-151.

Kandel ER, Segelbaum SA (200) Synaptic Integration. In: (Eds) Kandel ER, Schwartz JH, Jesse! TM, Principles of Neural Science, 4th Ed. Mcgraw-Hill, New York, pp. 212-214.

Kingery WS, Davies MF, Maze M (1997) Molecular Mechanisms for the analgesic properties of alpha-2 adrenergic agonists. In: Molecular Neurobiology of Pain. Process in Pain Research and Management vol. 9. (Ed) Borsook D. 1ASP Press, pp. 275-304.

Kotnik T, Miklavcic V (200) Second-<Jrder model of membrane electric field induced by altemating external electric fields. IEEE Transactions on Biomedical Engineering 47: 1074-1081.

Levine JD, Coderre T J, Basbaum AI (1988) The peripheral nervous system and the inflammatory process. In: Proceedings of the Vth World Congress on Pain. (Eds) Dubner R, Gebhart GF, Bond MR. Elsevier Science. pp. 33-43.

Li CL. Bak A (1976) Excitability of the A-and C-fibers in a peripheral nerve. Experimental Neurology 50:67-79.

Macdonald AJ R, Coates TW (1995) The discovery of transcutaneous spinal electroanalgesia and its relief of chronic pain. Physiotherapy 81: 653-661.

Mayer EA. Raybould H. Koelbel C (1998) Neuropeptides, inflammation and motility. Dig Dis Sci 33:71 S-77S.

Munglani R (1999) The longer tern effect of pulsed radiofrequency for neuropathic pain. Pain 80:437-439.

Nicholls JG, Martin AR, Wallace BG, Fuchs PA (2001 a) From Neuron to Brain. Sinauer Associates, Inc. Sunderland, Massachusetts, USA pp. 232-242.

Nicholls JG, Martin AR, Wallace BG, Fuchs PA (2001b) From Neuron to Brain. Sinauer Associates Inc., Sunderland, Massachusetts, USA. pp. 281-282.

Nicholls JG, Martin AR, Wallace BG, Fuchs PA (2001c) From Neuron to Brain. Sinauer Associates, Inc., Sunderland, Massachusetts, USA, p. 123.

Palmer ST, Martin DJ, Steedman WM, Ravey J. (1999) Alternation of Interferential current and transcutaneous electrical nerve stimulation frequency: effects on nerve excitation. Arch Phys Med Rehabil 80: 1065-1071.

Panagopoulous DJ, Messini N, Kararbounis A, Philippetis AL, Margaritis LH (2000) A mechanism for action of oscillating electric fields on cells. Biochemical and Biophysical Research Communications 272:634-640.

Panagopoulous DJ, Karabounis A, Margaritis LH (2002) mechanism for action of electromagnetic fields on cells. Biochemical and Biophysical Research Communications 298:95-102.

Peon C-S, Young DL, Siniaia MS (200) High-pass filtering of carotid-vagal influences on expiration in rat: role of N-methyi-D-aspartate receptors. Neuroscience Lettes 284:5-8.

Rang PH, Dale MM, Ritter JH (1998) Pharmacology. 3rd Ed. Churchill Livingstone, Edinburgh, London, New York, Philadelphia, Sydney, Toronto, pp. 620-622.

Shealy CN, Mortimer JT (1971) Dorsal Column Electroanalgesia. In: (Eds) Reynolds DV, Sjoberg AE. Neuroelectric Research. Charles C Thomas. pp. 146-150.

Sluijter ME (2001 a) Radiofrequency. Part 1: A Review of Radiofrequency Procedunas in the Lumbar Region. FlivoPress Sa, Switzerland. p. 51.

Sluijter ME, Cosman ER, Rittman II WB, van Kleef M (1998) The effects of pulsed radiofrequency fields applied to the dorsal root ganglion-a preliminary report. The Pain Clinic 2: 109-117.

Stein C, Schafer M, Cabot PJ, Zhang Q, Zhou L, Carter L (1997) Opioids and inflammation. In: (Ed) Borsook D. Molecular Neurobiology of Pain. Progress in Pain Research and Management vol. 9. IASP Press, pp. 25-43.

Stinus L, Auriacombe M, Tignol J. Limoge A, Le Moal M (1990) Transcranial electrical stimulation with high frequency intermittent current (Limoge's) potentiates opiate-induced analgesia: blind studies. Pain 42: 351-363.

Tanner KD, Gold MS, Riechling DB, Levin JD (1997) Transduction and excitability in nociceptors: dynamic 34 phenomena. In: (Ed) Borsook D. Molecular Neurobiology of Pain. Progress in Pain Research and Management., vol. 9, IASP Press, Seattle. pp. 79-105.

Towell AD, Williams D, Boyd SG (1997) High frequency non-invasive stimulation over the spine: effects on mood and mechanical pain tolerance in normal subjects. Behavioral Neurology, 10:61-65.

Ushida T, Tani T, Kawasaki M, Iwatsu 0, Yamamoto H (1999) Peripheral administration of an N-methyi-D-aspartate receptor antagonist (MK-801) changes dorsal hom neuronal responses in rats. (Erratum in Neurosci Lett 1999 260:210] Neuroscience Letters 260:89-92.

Duggan A.W. et al.. "Bicuculline and Spinal Inhibition Produced by Dorsal Column Stimulation in the Cat." Pain, 22:249-259 (1985).

Johnson M.I. et al., "An in-depth study of long-term users of transcutaneous electrical nerve stimulation (TENS). Implications for clinical use of TENS," Pain, 44:221-229 (1991).

Liu et al., :Activation of Na+ and K+ Pumping Modes of (Na,K)-ATPase by an Oscillating Electric Field, The Journal of Biological Biochemistry, 265:7260-7267 (1990).

Melzack et al., "Pain Mechanisms: A New Theory," Science, 150:971-979.

Salar et al., "Effect of Transcutaneous Electrotherapy on CSF B-Endorphin Content in Patients Without Pain Problems," Pain, 10:169-172.

Wall, "The Discovery of Transcutaneous Electrical Nerve Stimulation," Journal of Orthopaedic Medicine, 3:26-28 (1986).

Woolf, "Segmental afferent fibre-induced analgesia: transcutaneous electrical nerve stimulation (TENS) and vibration," The Texbook of Pain, 2nd Ed., Churchill Livingston, pp. 884-896.

* cited by examiner

ELECTROTHERAPY APPARATUS

CROSS-REFERENCE TO RELATED APPLICATION(S)

This application is a divisional of U.S. patent application Ser. No. 11/569,366, filed Dec. 20, 2006, which is a National Phase Patent Application of PCT/GB2005/002075, filed May 24, 2005, which claims the benefit of GB Patent Application GB0411610.9, filed May 24, 2004, all of which are incorporated herein by reference in their entirety.

BACKGROUND

The present invention relates to electrotherapy, and provides apparatus and methods for application of such therapy.

There are a number of electrotherapy techniques that induce action potentials. Aβ fibres have low thresholds that enable them to respond to such innocuous events as movement, vibration and light touch. Melzack and Wall 1965 and Wall 1986 described how analgesia could be produced when Aβ fibres are stimulated at 100 Hz, a frequency that none of the other sensory nerves can follow faithfully. Wall 1986 produced these effects by applying the current through needles inserted into the patient's nerves. To avoid the inconvenience and possible complications of inserting needles into nerves, he soon employed surface electrodes, leading to the term Transcutaneous Electrical Nerve Stimulation (TENS).

Woolf 1989 reviewed the use of these devices, and described their electrical parameters. The usual TENS machine develops a pulse, whose width can be varied from 50-500 µs, employing a current whose amplitude can be increased from 0-50 mA, and whose frequency is generally 100 Hz. The TENS pulse width (50-500 µs) is sufficiently long in duration to excite Aβ nerves at low voltage causing a painless tingling and stimulation of interneurones releasing GABA (Duggan et al 1985) that inhibits the release of SP within the spinal cord by C-fibres. Johnson et al 1991 showed that 'high intensity stimulation'; where the amplitude is increased sufficiently to recruit Aδ fibres, invokes release of met-enkephalin in the spinal cord which produces a more prolonged analgesic effect than that provided by the release of GABA produced by the more usual 'low intensity stimulation' of Aβ fibres. Salar et al 1981 observed opioids were released slowly into the cerebrospinal fluid when TENS is performed at frequencies of 40-60 Hz and at amplitudes of 40-80 mA: signals that readily recruit Aδ fibres, whose firing is associated with sharp pain.

To stimulate Aβ fibres, frequencies below 1 kHz are employed. The typical TENS device runs at 100 Hz. However the TENS frequency may be reduced still further to below 80 Hz.

As tissue impedance is capacitive, it tends to fall as frequency is increased. In order to increase tissue penetration, signals may be provided at a frequency where the intervals between each electric signal are less than the refractory periods of axons that require stimulation. In order to produce action potentials, such signals are modulated to provide low frequency stimulation either by interference or interruption.

The interference method of applying medium frequency currents is exemplified by Nemec U.S. Pat. No. 2,622,601, Griffith U.S. Pat. No. 3,096,768 and many others. Two signal sources are each connected to a pair of electrodes. They can produce an amplitude modulated medium frequency signal in the tissues called interferential current as follows. The first signal source uses a medium frequency carrier wave (typically 4.0 kHz) while the other operates at a slightly different frequency (typically 4.1 kHz). Their respective pairs of surface electrodes are arranged on the body in a manner that allows the two oscillating currents to meet in deep tissues where modulation produces interference or a beat frequency in the low frequency range typically at 100 Hz. This in turn is said to stimulate deeply placed Aβ fibres to produce analgesia.

As an example of the interrupted form of modulation, in order to avoid the surgical complications of implanting electrodes in direct contact with the brain, Limoge U.S. Pat. No. 3,835,833 and Stinus et al 1990 describe Transcutaneous Cranial Stimulation (TCES), an application of intermittent 4 ms trains of medium frequency current (typically 166 kHz) arranged so each pulse provided is 100 mA peak-to peak to a patient's head via one frontal cathode and two posterior anodes (one placed over each mastoid process). The positive going element of each pulse (67 mA) lasts 2 µs; while the negative going portion has a lower amplitude of 33 mA but lasts 4 µs. Each 4 ms train is repeated typically at 77 or 100 times per second. The medium frequency is employed to penetrate the tissues of the brain from surface electrodes. Stinus (1990) has observed that such stimulation only raised pain thresholds when opiates have been administered.

Macdonald and Coates GB 2290033, U.S. Pat. No. 5,776,170 explored the effects of applying signals whose pulse width is so brief, typically 4 µs, that the voltage gated channels lying in excitable membranes of peripheral nerve axons that lie in the path of the current do not have time to respond to these electric signals sufficiently to reach membrane threshold and produce action potentials. This form of electrotherapy produces analgesic and mood altering effects provided that surface electrodes are placed over the spinal cord. Macdonald and Coates 1995 called this method TSE (Transcutaneous Spinal Electroanalgesia). Towell et al 1997 performed a controlled trial that demonstrated TSE produces beneficial changes in mood provided the electrodes are placed over the spinal cord.

GB2290033 states that as frequency is increased the voltage has to be reduced. The document quotes 150V as being a sufficient voltage at 5 kHz and 25V as being sufficient at 150 kHz.

The present invention provides methods and apparatus related to electrotherapy, which address certain limitations or disadvantages of the prior art.

In a first aspect, the present invention provides an apparatus for producing analgesia in a patient through electrical signals applied by electrodes to the patient's body, the apparatus comprising electrodes for application to the patient's body and a signal generator which is connectable to the electrodes, wherein the signal generator is arranged to generate a biphasic waveform comprising successive cycles each containing a positive and negative pulse, wherein the mean pulse width $P_w$ is less than 10 µs, and wherein $V_p^2 \cdot Pw \cdot F_p$ is at least 200, where $V_p$ is the mean pulse voltage, and $F_p$ is the number of forward and reverse pulses per second.

In this application, references to waveform are to an electrical waveform. The term "pulse" refers to either the positive or negative (forward or reverse) element of the biphasic waveform. Hence the pulse voltage is the amplitude (V) of the positive or negative pulse and the pulse frequency is the number of forward and reverse pulses per second, counting both. The pulse width Pw is measured in seconds.

A cycle consists of both a forward and reverse pulse. Therefore, the number of forward and reverse pulses per second (the pulse frequency) will be equal to twice the cycle frequency. The leading edge of the cycle can be either positive or negative. Normally, the leading pulse in each cycle will be of the same polarity, but this is not essential.

It has been found that the apparatus as described above can be used to deliver a high power treatment to a patient. This may be done without generating action potentials in sensory nerves at a level that might be uncomfortable (as would be the case for example with a TENS pulse).

It has also been found that embodiments of the present invention are capable of treating surprisingly large volumes of tissue, and/or treating deep structures more effectively than the prior art. Moreover, unlike conventional TSE treatment, it has been found that treatment is possible by applying the electrodes to the body at points which provide current flow in the region of the affected area, and not necessarily over the central nervous system. Among other things, this has been found to be helpful in reducing inflammation, which can for example be used to treat inflammatory arthritic and visceral disease.

The present waveform is referred to herein as a "HPSP" (high power short pulse) waveform. The relationship $V_p^2 \cdot Pw \cdot F_p \geq 200$ is derived from consideration of the power which can be applied to the patient. The mean power dissipation can be approximated to $W_m = Pw \cdot F_p \cdot V_p^2 / Z$ where $W_m$ is the mean power dissipation and Z is the impedance of the tissues and connecting means to the device (electrodes and leads). This aspect of the invention provides a greater power level for a given load impedance than was employed or suggested in the prior art. For example, at with signals applied that contain most energy in harmonics at frequencies of at least 20 kHz, the load impedance of the human body can be approximated at a constant 150Ω. Based on this, the maximum power taught by GB2290033 is 1.125 W. The present invention operates significantly above this level.

The relationship $V_p^2 \cdot Pw \cdot F_p \geq 200$ is equivalent to and can also be expressed as $V_{RMS} \geq \sqrt{200}$.

The high RMS value of the applied voltage when compared with other electrotherapy techniques produces similarly high RMS currents in the patient. For example, at $V_{RMS} = \sqrt{200}$, the RMS current with a 150 Ω load (typical of a patient) would be 94 mA, which is six times higher than what is generally accepted to be a strong TENS signal of 15 mA.

$V_p^2 \cdot Pw \cdot F_p$ may be at least 220, preferably it is at least 250, 340 or 500.

Due to heating effects at higher powers, it may be preferred that $V_p^2 \cdot Pw \cdot F_p$ is below 1800, more preferably below 1200.

Preferably, the biphasic waveform is continuous. By a "continuous" biphasic waveform is meant a series of cycles in which the leading pulses are equally spaced.

The mean pulse width for the forward and reverse pulses, and preferably the pulse width of each of the forward and reverse pulses, may be 6 μs or less, 4 μs or less, e.g., 3 μs, 2 μs, 1.5 μs, 1 μs, 0.75 μs or less, and optionally at least 0.01 μs, 0.05 μs, or 0.5 μs. In some embodiments, short pulse widths are preferred so as to increase the rate of change of the electrical field, e.g., for a given mean modulus or RMS current in the tissues.

Without wishing to be bound by theory, the inventors believe increasing the rate of change of the electrical field may increase coupling to cellular structures involved in transmission of pain. The signal penetrates deep tissues, and it is believed that it may produce beneficial effects by producing changes that affect one or more processes that occur in the central and or peripheral nervous systems, for example the behaviour of microtubules, the rate of release of certain ligands and or the responses to them by various ligand gated receptors. The signal may also have effects on the mobility of ions associated with the transmission of action potentials and act directly on other cell structures such as voltage gated channels in both the peripheral and central nervous system.

In some embodiments of the invention, it is preferred that the mean pulse voltage, and preferably the voltage of each positive and negative pulse, is at least 100V, preferably 150V and more preferably 200V. Optionally, the mean pulse voltage and/or voltage of each pulse has an upper limit of 500V, 400V, 300V or 250V, e.g., to meet safety requirements.

While all combinations of preferred voltages and pulse widths are specifically included, optionally, when the voltage (mean value or voltage of each pulse) is at least 100V, the pulse width (mean value or width of each pulse) is 6 μs or 4 μs or less; when the voltage is at least 150V the pulse width is 3 μs or less; and when the voltage is at least 200V the pulse width is 1.5 μs or less.

The pulse frequency (i.e. the number of forward and reverse pulses per second) may be at least 1000 Hz or 1200 Hz, more preferably at least 5 KHz, and still more preferably 10 KHz, 20 KHz or above.

The pulse frequency may be less than 2 MHz, more preferably less than 1 MHz or 500 kHz, still more preferably less than 250 kHz or 100 kHz.

It is preferred that the duty cycle (the ratio of "on time" to "off time") through one complete cycle should be less than 10% or 5%, preferably less than 2% or 1%, and greater than 0.1%, particularly where the biphasic wave is continuous.

Each pulse in the biphasic wave preferably has a rapid rise and fall phase, e.g., is substantially rectangular, subject to capacitor droop. Preferably the edge rate exceeds 250V4 μs, more preferably 500V/μs or 1000V/p.

Preferred embodiments of invention have a high pulse current during the pulse "on" time. For example the waveform may have a pulse current of at least 0.3 A throughout the pulse period. The current may vary over the pulse period due to capacitor droop, and may for example be 0.7 A-3 A at the start of the pulse, falling to 0.5 A to 2 A at the end of the pulse. The mean modulus current flowing through the patient is preferably at least 3 mA, preferably at least 6 mA and more preferably at least 10 mA. When measured at 150 ohm load, $V_{RMS} = \sqrt{200}$ gives an RMS current of 94 mA.

The present inventors have found that sensation can be obtained with the wave form used in embodiments of the present invention. The inventors measured the threshold of sensation produced by a biphasic square wave, that is, the point at which sensation is first felt. While the voltage threshold of sensation was affected by the pulse width, it was substantially unaffected by the frequency. Unexpectedly, therefore the threshold of sensation is not affected by the RMS or mean modulus current. Moreover, sensation can be provided at pulse frequencies well above the physiological limits, those frequencies greater than that which Aβ fibres can faithfully follow, for example 800 Hz to 1200 Hz.

It has furthermore been found that the threshold of sensation can be varied by varying the interpulse spacing. As the interpulse spacing is reduced, the voltage at which sensation is first perceived for a given pulse width increases, particularly for pulse widths below 4 μs. This allows the level of sensation to be varied independently of the power level or current supplied by the device or the associated rate of change of the electrical field in the tissues. In some embodiments it may be desirable to reduce the level of sensation that is felt, so that there is low or no sensation, e.g., allowing the patient to sleep when the device is operating. Alternatively, it may be desirable to provide a mild sensation, as this can be comforting to the user, and can help to distract from aches and pains. It is also believed that some mild tingling might play a role in expression of neurotransmitters.

It may be preferred that the mean pulse width, and more preferably the pulse width of each forward and reverse pulse, is less than 4 µs, to improve the ability of the sensation level to be varied with the interpulse spacing.

The interpulse spacing may be less than 4 µs, preferably less than 3, 2 or 1 µs and most preferably 0 µs. In some embodiments, a low interpulse spacing may be used together with a low pulse width (mean value or value per pulse), e.g., a pulse width of 2 µs or less, more preferably a pulse width of 1.5 µs or 1 µs or less, to provide mild or no sensation even at high voltages (i.e., peak pulse voltages), such as greater than 150V, 200V or 250V. Without wishing to be bound by theory, it is believed that a low interpulse space and preferably an interpulse space of 0 µs may also be beneficial because it provides a high rate of change in the electrical field per pulse.

In other embodiments, e.g., where some sensation may be desirable, the interpulse spacing may be at least 5 µs, preferably at least 6, 7, 8, 9 or 10 µs.

The interpulse spacing may also be varied to alter the wave harmonics. Without wishing to be bound by theory, the present inventors believe that the harmonic content of the wave is important in determining its treatment efficacy. For instance, the continuous wave form which is preferred in this aspect of the invention produces a series of harmonics at frequencies spread widely over the spectrum, when compared to a burst wave form in which most of the wave energy is concentrated around a narrow peak.

The inventors have compared the harmonic components of a square wave of 2 µS pulse width with equal positive and negative pulses and zero inter pulse space, with a square wave of the same pulse width with 2 µS inter pulse space, both at a cycle frequency of 20 kHz. The spacing between components in both cases was 20 kHz, but the waveform with 2 µS inter pulse space has its peak at approximately half the frequency of the waveform with zero space.

The inventors also examined a square wave of 2 µS pulse width with cycle frequency of 5 kHz and inter pulse spacing of 100 µS; in this case the return pulses are equally spaced between the forward pulses. This provides an interesting result with two distinct curves made up of harmonic components of the signal. One could be said to represent the harmonic components of the cycle frequency and the other the components of the pulses themselves. This dual curve structure may be desirable in increasing the chance of exciting resonance in the cellular structures, regardless of natural variation between them, e.g., in orientation. Hence, in some embodiments, it may be desirable for the interpulse spacing to be at least 20, 40, 60, 80 or 100 µs, up to half the distance between cycles.

Preferred HPSP pulses range from 4 µS width with the main harmonic components of this centred around approximately 125 kHz, through to 0.05 µS or less, equivalent to 10 MHz, and incorporate pulse frequencies varying in the range 1200 Hz through to 2 MHz.

Selection of inter pulse space and pulse width therefore plays a primary role in determining the range of frequencies provided by the therapy.

HPSP therapy can be considered to be a form of radio frequency stimulation of the tissues with a much wider spread of harmonics than that associated with the known types of pulsed and continuous radio frequency electrotherapy in use today. The waveform parameters can be selected to deliver oscillating electric fields in the ranges of 1 kHz to 20 MHz or more. The region covering 50 kHz to 1 MHz (harmonics in fields) is thought to be that at which effects on cell structures and ion mobility are maximised and therefore this is the preferred range of frequencies that are employed.

Kotnik et al 2000 explored the degree of amplification of an external electric within the cell at various harmonic frequencies and showed the cell membrane amplifies externally applied alternating current electric fields by a factor of several thousands provided the harmonic frequency is 100 kHz or less. As harmonic frequency is increased above 100 kHz, this amplified effect greatly decreases, and the capacitive properties of structures contained within the cell and extracellular fluid become increasingly important. Liu et al 1990, studied the effects of oscillating electric fields on the activation of Na+ and K+ pumping modes of (Na,K)-ATPase. This is an active transport system (energised by the hydrolysis of ATP) in the membrane for regulating the extrusion of Na+ and influx of K+ ions into the cell (the sodium pump) either to maintain cellular electrolyte balance or provide action potential transmission. At a voltage of 20V/cm, various frequencies were tested and uncoupled transport modes were shown at two frequencies; increased influx only was observed at 1 kHz; while increased efflux only was observed at higher frequencies particularly 1 MHz.

In another aspect, the apparatus as described above can be used in a method of inducing analgesia in a patient, the method comprising applying the electrodes to the patient's body, and providing a waveform as described.

In another aspect of the invention, there is provided an apparatus for producing analgesia in a patient through electrical signals applied by electrodes to the patient's body, the apparatus comprising electrodes for application to the patient's body and a signal generator which is connectable to the electrodes, wherein the signal generator is arranged to generate a biphasic waveform comprising successive cycles each containing a positive and negative pulse, and wherein the apparatus comprises a control element for varying the spacing between the positive and negative pulse.

The mean pulse width, and preferably the width of each positive and negative pulse of the biphasic waveform, is preferably less than 4 µs, to maximise the ability to vary sensation by varying the interpulse spacing, and optionally at least 0.5 µs or 2 µs. Preferably, the control element for varying the spacing between the positive and negative pulse is able to vary the interpulse spacing between 0 µs and half of the cycle time, more preferably 0 µs and 20 µs or 0 µs and 10 µs.

This apparatus may be particularly beneficial at high mean pulse voltages, e.g., at least 100V, 150V or 200V where sensation is more likely to be experienced. More preferably, these voltages refer to the voltage of each pulse. Optionally, $V_p^2 \cdot Pw \cdot F_p$ is at least 200 and/or less than 1200 or 1800. It may also or alternatively be preferred that pulse frequency is at least 1000 Hz or 1200 Hz, more preferably at least 5 kHz, and still more preferably 10 KHz, 20 KHz or above. The pulse frequency may be less than 2 MHz, more preferably less than 1 MHz or 500 kHz, still more preferably less than 250 kHz or 100 kHz. In some embodiments, the wave form may be a HPSP waveform, as above.

The control element may be operable by an operator, e.g., the user, for example so that the user can set the interpulse spacing to a level which provides a comfortable level of sensation.

Alternatively, the control element may provide automated variation of interpulse spacing, for example rhythmical modulation, or automated random modulation, e.g., in a series of modulation cycles. This may be of particular benefit at modulation rates below 1200 Hz, preferably modulation rates below 100 Hz or 50 Hz, and/or greater than 0.25 Hz, so as to modulate the sensory nerves within the physiological range. Moreover, since the carrier signal can be applied at well above the physiological range and with high peak voltages it may be of particular benefit when the power levels are fairly high so as to penetrate large volumes of tissues.

The control element may be for example a suitably programmed processor, a manual control or circuit adapted to provide a rhythmic or automated random modulation.

In some embodiments, the apparatus (preferably an apparatus having automated variation in the interpulse spacing) also comprises a control for varying the pulse voltage or pulse width or both, for example a control which would allow the base level of sensation to be set by the user.

In another aspect, the present invention provides a method of inducing analgesia through electrical signals applied by electrodes to the patient's body, wherein the induction of analgesia comprises
providing an apparatus comprising electrodes for application to the patient's body and a signal generator connected to said electrodes, wherein the signal generator is arranged to provide a biphasic electrical waveform comprising successive cycles each having a positive and negative pulse,
applying the electrodes to two or more locations on the patient's body;
and providing said biphasic electrical waveform;
and wherein the spacing between the positive and negative pulse is modulated during the treatment.

The spacing between the positive and negative pulse can be modulated so as to alter the level of sensation experienced by the patient during the treatment.

In some embodiments, it may be preferred that the method comprises adjusting the interpulse spacing such that no sensation is felt, except optionally for a transient sensation which quickly fades. In other embodiments, it may be preferred that the interpulse spacing is adjusted to provide the user with mild sensation. For example, this can be reassuring to the user.

The modulation may take place one or more times during the treatment to achieve a desired sensation level, or may be ongoing or repeated, e.g., in a series of modulation cycles.

The modulation of interpulse spacing may also have beneficial treatment effects, for example, it may aid the expression of neurotransmitters or aid relaxation.

In preferred embodiments, the modulation is repeated during the treatment, e.g., randomly or rhythmically. The modulation rate of the interpulse spacing may preferably be below 1200 Hz, more preferably below 100 Hz or 50 Hz, and/or greater than 0.25 Hz, so as to modulate the sensory nerves within the physiological range. Preferably, the user experiences at least some sensation.

This method preferably allows use of a high voltage, high current signal which may penetrate deep tissues more effectively than a typical TENS pulse and then modulating the signal by varying the inter pulse spacing in such a way that action potentials are generated in deep nerves at interpulse spacing modulation rates well within the physiological range, preferably 0.25 Hz to 0.5 Hz to 50 Hz or 120 Hz.

In each of the above methods, the spacing can be modulated automatically, e.g., rhythmically (i.e. with an identifiable pattern even a complex one) or randomly, e.g., under control of a microprocessor, or via a manual control. When the method provides a particular, desired level of sensation, it may be preferred that the spacing is modulated by a manual control and/or a control which is operable by a user. In other embodiments, an automated control may be preferred. A random modulation may help in reducing adaption to the signal.

Each of the above methods may also comprise selecting the base level of sensation by adjusting the voltage or pulse width or both. For example, the base level may be selected such that the user experiences a transient sensation, e.g., at an interpulse spacing of 0 µs. Optionally, in setting the base level of sensation, the pulse width may be varied, and the pulse voltage maintained at a value of greater than 150, 180V or 200V. Modulation of the interpulse spacing may then give a good correlation between sensation and interpulse space.

In another aspect, the present invention provides a method for pre-setting the operating parameters of an apparatus for producing analgesia in a patient through electrical signals applied by electrodes to the patient's body, the apparatus comprising electrodes for application to the patient's body and a signal generator which is connectable to said electrodes, wherein the signal generator is arranged to provide a biphasic waveform comprising successive cycles each having a positive and negative pulse, the method comprising
selecting the voltage and pulse width, and
selecting the interpulse spacing with reference to a predetermined relationship between sensation and interpulse spacing at said voltage and pulse width.

In each of the above methods, preferred operating conditions and parameters of the waveform are as described for the above apparatus, comprising a control element for varying the spacing between the positive and negative pulse.

In another aspect, the present invention provides an apparatus for producing analgesia in a patient through electrical signals applied by electrodes to the patient's body, the apparatus comprising electrodes for application to the patient's body and a signal generator which is connectable to said electrodes, wherein the signal generator is arranged to provide a biphasic waveform comprising successive cycles each containing a positive and negative pulse, wherein the mean pulse width $P_w$ is less than 1.5 µs and the spacing between the positive and negative pulse is between 0 µs and 2 µs.

Preferably, the mean pulse voltage (more preferably the voltage of each pulse) is at least 130V, more preferably at least 150V or 170V.

It may be preferred that the interpulse spacing is 1.5 µs or less, in which case the voltage (mean or voltage of each positive and negative pulse) may be at least 140V, preferably at least 160V or 180V. Still more preferably, the interpulse spacing may be 1 µs or less, in which case the voltage may be at least 180V, preferably at least 200V, more preferably at least 220V. An interpulse spacing of 0.5 µs or less, or 0 µs may be preferred in some embodiments. For example, a zero interpulse spacing may be advantageous in providing a high rate of change of the electrical field per pulse.

Preferably, the mean pulse width and preferably the width each pulse is less than 1.5 µs, more preferably less than 1.25, 1 µs or 0.75 µs.

In some embodiments, the pulse frequency may be at least 1000 or 1200 Hz, more preferably at least 5 kHz, 10 kHz or 20 kHz, and/or less that 2 MHz, 1 MHz, 500 kHz or 250 kHz. Optionally, $V_p^2 \cdot Pw \cdot F_p$ is at least 200 and/or less than 1200 or 1800.

In another aspect the present invention provides a method of inducing analgesia in a patient's body through electrical signals applied by electrodes to the patient's body, using an apparatus comprising electrodes for application to the patient's body and a signal generator which is connectable to said electrodes, wherein the signal generator is arranged to generate a biphasic waveform comprising successive cycles each containing a positive and negative pulse, the method comprising:
applying the electrodes to two or more locations on the patient's body such that at least one of said locations on the patient's body does not overlie the central nervous system;
providing said biphasic electrical waveform so as to induce analgesia at said site.

Preferably, said two or more locations do not overlie the central nervous system, i.e., brain or spinal cord. More preferably, at least one location is not in the immediate vicinity of the spinal cord, for example is not on the neck, and/or is located more than 10 or 15 cm laterally from the spine and/or on the ventral side of the body. The locations preferably span, i.e., are above and below or on either side of, the area of pain or discomfort, and/or peripheral nerves conducting signals from said area of pain or discomfort. They preferably provide current through an area which includes the area of pain or discomfort, and/or peripheral nerves conducting signals from said area of pain or discomfort. For example, at least one location may be on or in the region of a limb (arm or leg including the hand or foot), the abdomen or the face.

The method of inducing analgesia may be a method of relieving pain or discomfort associated with chronic or acute conditions. For example, it may be a method of relieving pain or discomfort associated with physical injury (including postoperative pain, fracture, bruising, muscle strain and the like), or with chronic or acute diseases or disorders.

Said method may preferably be a method of relieving pain or discomfort associated with inflammatory conditions, particularly rheumatoid arthritis, and other inflammatory arthritic and visceral conditions. The method may also be a method of treating said conditions.

Preferably, the mean pulse width, and more preferably the width of each pulse, is less than 10 μs, more preferably 6 μs or less, 4 μs or less, more preferably 3 μs, 2 μs, 1.5 μs, 1 μs, 0.75 μs or less. It may be preferred that the mean voltage and preferably the voltage of each pulse is at least 100V, preferably at least 150V or 200V.

While all combinations of preferred voltages and pulse widths are specifically included, optionally, in certain embodiments, when the voltage (mean value or voltage of each pulse) is at least 100V, the pulse width (mean value or width of each pulse) is 6 μs or 4 μs or less; when the voltage is at least 150V the pulse width 3 μs or less; and when the voltage is at least 200V the pulse width is 1.5 μs or less.

The pulse frequency may be at least 1200 Hz, more preferably at least 5 kHz, and still more preferably 10 kHz, 20 KHz or above, and/or less than 2 MHz, 1 MHz, 500 KHz, 250 kHz or 100 KHz.

Optionally, $V_p^2 \cdot Pw \cdot F_p$ is at least 200 and/or less than 1200 or 1800. In some embodiments, the waveform is a HPSP waveform, as described above.

In another aspect, the present invention comprises a method of selecting treatment parameters during the induction of analgesia through electrical signals applied by electrodes to the patient's body, wherein said therapy comprises: providing an apparatus comprising electrodes for application to the patient's body and a signal generator connectable to said electrodes, wherein the signal generator is arranged to generate a biphasic waveform comprising a successive cycles each containing a forward and reverse pulse, applying the electrodes to two or more locations on the patient's body;

and providing said waveform at a starting voltage and pulse width;

the method of selecting treatment parameters comprising varying the voltage and/or pulse width until the patient experiences a comfortable level of sensation, and selecting the voltage and pulse width at which comfortable sensation is felt.

Preferably, the method comprises varying the pulse voltage, e.g., so that the mean pulse voltage and preferably the voltage of each pulse is varied within the range of 0-500V, preferably 0-250V, 200V or 150V.

The starting pulse width (mean value and preferably also value for each pulse width), may be 10 μs or below, most preferably 4 μs or below. It is preferably varied in the range of 0.01 μs, 0.05 μs or 0.5 μs to 4 μs or 10 μs.

Optionally, the method also comprises providing the waveform at a starting interpulse spacing, and varying the interpulse spacing, e.g., in the range of 0 μs-20 μs, preferably in the range of 0 μs-10 μs. In this embodiment, the starting pulse width (mean value and preferably also value for each pulse width) may be 4 μs or less.

The pulse frequency may be greater than 1200 Hz, more preferably at least 5 kHz, and still more preferably 10 kHz or 20 KHz or above.

In a preferred embodiment, the method comprises a further step of, after selecting the voltage and pulse width at which comfortable sensation is felt, increasing the number of pulses per second $F_p$ such that $F_p$ is at least $200/(V_p^2 \cdot Pw)$ but preferably less than $1800/(V_p^2 \cdot Pw)$ or $1200/(V_p^2 \cdot Pw)$. Preferably, $F_p$ is at least $300/(V_p^2 \cdot Pw)$ or $400/(V_p^2 \cdot Pw)$.

In some or all of the aspects of the invention described above, it may be preferred each pulse of the biphasic waveform has fast rise and fall, e.g., is substantially rectangular, subject to capacitor droop. It may have an edge rate of 250V/μs or above, more preferably 500V/μs or 1000V/μs or above.

In some or all of these aspects, the biphasic waveform may be a "burst" waveform comprising a train a multiple pulses followed by a quiet period. However, it may be preferred that it is a continuous wave form, in which case it is preferred that the duty cycle (the ratio of "on time" to "off time") through one complete cycle is preferably be less than 10% or 5%, more preferably less than 2% or 1%, and preferably greater than 0.1%.

It may also be preferred that the amount of electrical charge in the forward and reverse pulse is equal. This gives a mean current of zero, and helps to minimise ionic transport. Conveniently, this can be achieved by having a forward and reverse pulse of equal voltage and pulse width. If the amplitude (voltage) or pulse width is not equal for the forward and reverse pulse, then the mean value for the two pulses is calculated. In the case where it is desired the amplitude or pulse width of the second pulse is not the same as the first pulse, then the parameters of the second pulse are preferably adjusted so the mean value of the voltage applied to the patient is zero.

It may further be preferred that the apparatus for providing analgesia in a patient comprises a single signal generator arranged to produce one biphasic waveform. Similarly, it is preferred that some or all of the methods comprise the provision of a single biphasic waveform from a single signal generator. If more than one waveform is provided by the apparatus/method, then it is preferred that these waveforms are of the same cycle frequency, or that one is an integer multiple of the other to reduce interference effects.

A difficulty with treatment methods which involve imparting relatively high power to the patient is that safety mechanisms must be put in place which prevent a dangerous level of charge from being applied in the event of malfunction. This is also a concern in an apparatus in which variable frequency, pulse width and voltage can be applied.

There are two international safety standards of particular relevance, these are IEC 60601-2-10, "Particular requirements for the safety of nerve and muscle stimulators" and the US standard AAMI NS4-1985 (Transcutaneous Electrical Nerve Stimulation).

Key safety requirements of 60601-2-10 are:
Maximum limits on output current (rms) are 80 mA at DC, 50 mA at 400 Hz, 80 mA at 1500 Hz and 100 mA above 1500 Hz (with a 500 ohm resistive load).
The maximum pulse energy should not exceed 300 mJ.
The peak output voltage should not exceed 500V.

AAMI NS4 is being revised and its American National Standard status has been withdrawn because it is more than 10 years old. It however remains an AAMI (Association for the Advancement of Medical Instrumentation) standard and is the most directly relevant published document for the design of TENS devices. The key requirements of NS4 are:

Resistive loads of 200 Ω, 500Ω and 1 kΩ are defined as the test loads. 500Ω resistive is considered as the reference waveform for safety purposes.
The minimum output for efficacy (with the controls at maximum) is either 7 µC per pulse or a complex waveform whose average stimulating component amplitude is at least 0.5 mA into a load of 500 Ω.
The maximum charge per pulse should under no circumstances exceed 75 µC into a 500Ω load.
Maximum average current shall not exceed 10 mA, the limit for DC currents to reduce burns due to ionic transport.

In GB 2 290 033, it is suggested that a capacitor could be placed in series with one of the electrodes to isolate the patient from the possibility of direct current stimulation. However, such an arrangement is not suitable for producing square wave shaped pulses.

In a further aspect, the present invention provides an apparatus for producing analgesia in a patient through electrical signals applied by electrodes to the patient's body, the apparatus comprising electrodes for application to the patient's body and a signal generator which is connectable to the electrodes, wherein the signal generator is arranged to generate a biphasic waveform comprising successive cycles each containing a positive and negative pulse, and comprises:

a converter for producing a desired voltage from a power supply;
a first capacitor which is in electrical connection with said converter and which is arranged to provide the positive pulse to one of said electrodes;
a second capacitor which is in electrical connection with said converter and which is arranged to provide the negative pulse to one of said electrodes;
wherein said first and second capacitors are respectively connected to an output by a corresponding pathway, the pathways including respective switches, and wherein the signal generator includes a controller arranged to control the operation of the switches to cause alternate discharge of the first and second capacitors through the corresponding pathway to generate said positive and negative pulses.

This apparatus may thus be operable so that it cannot generate a sustained harmful average current, particularly where the converter produces a desired voltage but is limited in current output, so that it cannot generate a dangerous current during the pulse time either by itself or in combination with the capacitors, nor deliver a pulse of more than the safety value in the even of either software failure or single component failure.

An advantage of this apparatus is that a key safety measure limiting the amount of charge which would be applied to the patient in the event of malfunction is present in the hardware.

The inventors have realised that in order to limit the current which can be supplied in the event of malfunction to an acceptable level, it is desirable that sum total of the charge transferred in the positive and negative cycles plus the current which can be supplied by the converter over the pulse period should not exceed a dangerous level. Preferably, it does not exceed a maximum of 75 µC, e.g., even under fault conditions.

As a result of these considerations, there is a limit on the rate that charge can be delivered from the converter and/or on the amount of charge which can be stored in the capacitors. As a result, there may be a significant droop in voltage over the pulse period, particularly for pulses of longer duration.

In the present apparatus, the wave is produced by discharging two independent capacitors fed from a common converter, one providing the positive pulse and one providing the negative pulse. This produces a wave which is substantially symmetrical in nature, since any voltage drop over the course of the capacitor discharge affects the positive and negative pulse to the same extent.

The converter is preferably adapted to produce the desired voltage from a battery, though it may also be adapted to produce the desired voltage from the mains supply as an additional or alternative source. The apparatus may optionally include a suitable battery, e.g., a rechargeable battery.

In a preferred embodiment, the signal generator produces an output which has a fast rise and fall phase, e.g., is substantially rectangular.

The output may have a pulse current (i.e., a peak pulse current) of greater than 1 A, 1.5 A or 2 A or 3 A. It may optionally be preferred that the output $V_p^2 \cdot Pw \cdot F_p > 200$. In some embodiments, the output will be a HPSP wave, as described above.

It is preferred that the capacitance of the capacitor decreases with voltage. This improves the ability of the device to be with a wide voltage range, storing only a safe level of charge at a high voltage but also storing enough charge at a low voltage to deliver effective stimulation with longer pulses, which are necessary at lower voltages. Ceramic type capacitors are particularly preferred.

In a preferred embodiment, when no output from the capacitor is desired, i.e. during the pulse off time, switches in the pathway connecting each capacitor to the output are turned off and an additional switch or switches are operated to short the patient outputs together either directly or via device OV. Preferably, the apparatus includes a control to control the operation of said switches. This helps to provide a rapid return of the trailing edge of the pulse to zero. Preferably, the edge rate is greater than 250 V/µs, more preferably greater than 500V/µs or 1000V/µs.

In preferred embodiments, further control and safety systems are provided. For example, pulse width may be controlled and/or limited by one, two or more independent systems. For example, pulse width can be limited by a logic circuit and/or by output transistors which cannot remain in the "on" state for more than a fixed period without edge transitions on the gate drives. The latter also protects against a microprocessor failure since the microprocessor may be expected to fail with its outputs in a frozen state.

By careful selection of the capacitor rating and the use of pulse "on time" limiting controls (such as circuitry in the switch drive logic, and level translation circuitry) the apparatus can be designed with a wide range of pulse and output voltage where the therapeutic pulse charge does not exceed 25 µC per pulse under normal operating conditions, and 75 µC per pulse under single or double fault conditions.

The signal generator may also include one, two or more independent means of monitoring the signal, for example monitoring the current and/or voltage produced by the apparatus. These may include means for measuring the output current from the converter (wherein the measured current may be fed back into hardware circuitry in the converter to provide either a current limit or a current control loop and/or fed into a microprocessor for monitoring processes), means for measuring the current from one or both capacitors, and/or a means for measuring the voltage and current applied to the patient.

Preferably, said first and second capacitors are respectively connected by a corresponding pathway to an output path to the patient. Means for monitoring this signal may preferably be located in the output path. Alternatively, if electronically more convenient, it may be located in the in the return pathway from the output since this is at device 0V potential and therefore does not require translation of the signal from the output sensor.

Preferably, the device includes a safety device which operates to discharge the capacitors to device 0V in the event that the voltage in either pathway and/or the output current exceeds a predetermined limit, e.g., as detected by monitoring circuits implemented in hardware. Most preferably, this device is a Silicon Controlled Rectifier (SCR). In preferred embodiments, the device should also be operable by a microprocessor in the event of an error or shutdown identified by the microprocessor.

Preferably, the apparatus comprises at least two independent circuits for monitoring the voltage and/or current produced by the apparatus and also comprises means for comparing the measured values, thus enabling an error in either circuit to be detected, and optionally causing shutdown of the device.

Means for monitoring and/or comparing the signal and/or controlling discharge of a pathway should preferably be implemented in hardware and conveniently may also be implemented using a microprocessor as backup.

While aspects of the invention have been discussed independently, they may also be used together in any combination.

In the above aspects of the invention, the electrodes of the device may be either surface electrodes or implanted electrodes. References to the application of an electrode to a location on the patient's body are to be construed accordingly to include electrode implantation. Normally, implanted electrodes are covered with insulating material except at their tip, but this is not essential.

Specific embodiments of certain aspects of the present invention will now be described in more detail with reference to the figures. These are provided by way of explanation and example, and are not to be construed as limiting.

BODY IMPEDANCE AND POWER DISSIPATION

Using stainless steel mesh electrodes of size 50×50 mm, the inventors made various measurements of the impedance between electrodes across the following positions: a) on the forearm over the median nerve with the centre of electrodes 170 mm apart; b) on the posterior aspect of the thorax with electrodes over the spine at T1 and T12 and, c) across the neck with the electrodes positioned just below the mastoid processes.

These measurements are subject to error since the measured impedance can move up to +/−6 dB by changes in adhesion of the electrodes for example. The measurements are also changed by using different electrode types. However, with good quality electrodes using a stainless steel mesh substrate and careful application techniques the impedance varies a surprisingly small amount with different electrode locations on the body, provided the measurements are made on the subject over a short period of time.

Figure 3:
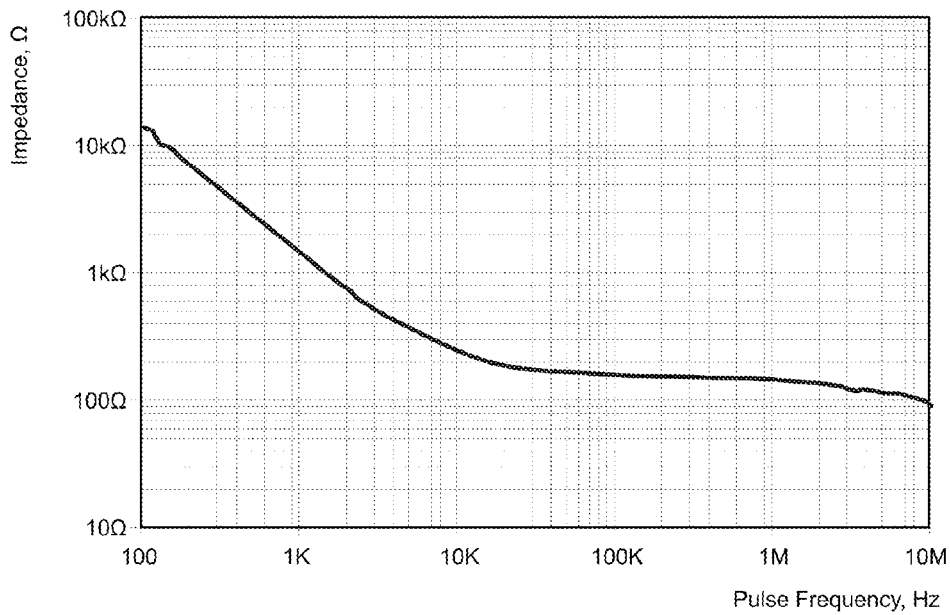
FIG. 3 shows a body impedance measurement taken over the median nerve.
Figure 4:
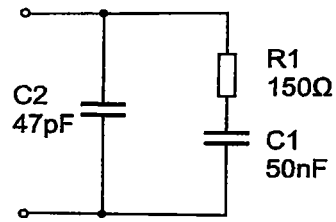
FIG. 4 shows a body equivalent circuit including lead capacitance and electrodes.

FIG. 3 shows a graph of impedance of the tissues measured over the median nerve as described above. As a useful approximation, the impedance looks like a series R-C combination, as shown in FIG. 4. R1 and C1 represent the tissues and C2 represents the capacitance of the leads and electrodes. C2 causes the slight fall off at frequencies approaching 10 MHz, this is seen by the apparatus but can be neglected for practical considerations. A parallel resistor of high value could be added to the equivalent circuit to simulate the DC body DC resistance, although this is several MΩ and can therefore be neglected. By inspection of the graph, the tissues can be considered to be primarily resistive above 21 kHz in the example shown. Typical values for resistance are 150Ω along the forearm and between T1 and T12 on the spine and 120Ω across the neck, measured with stainless steel mesh conductor electrodes.

Figure 5:
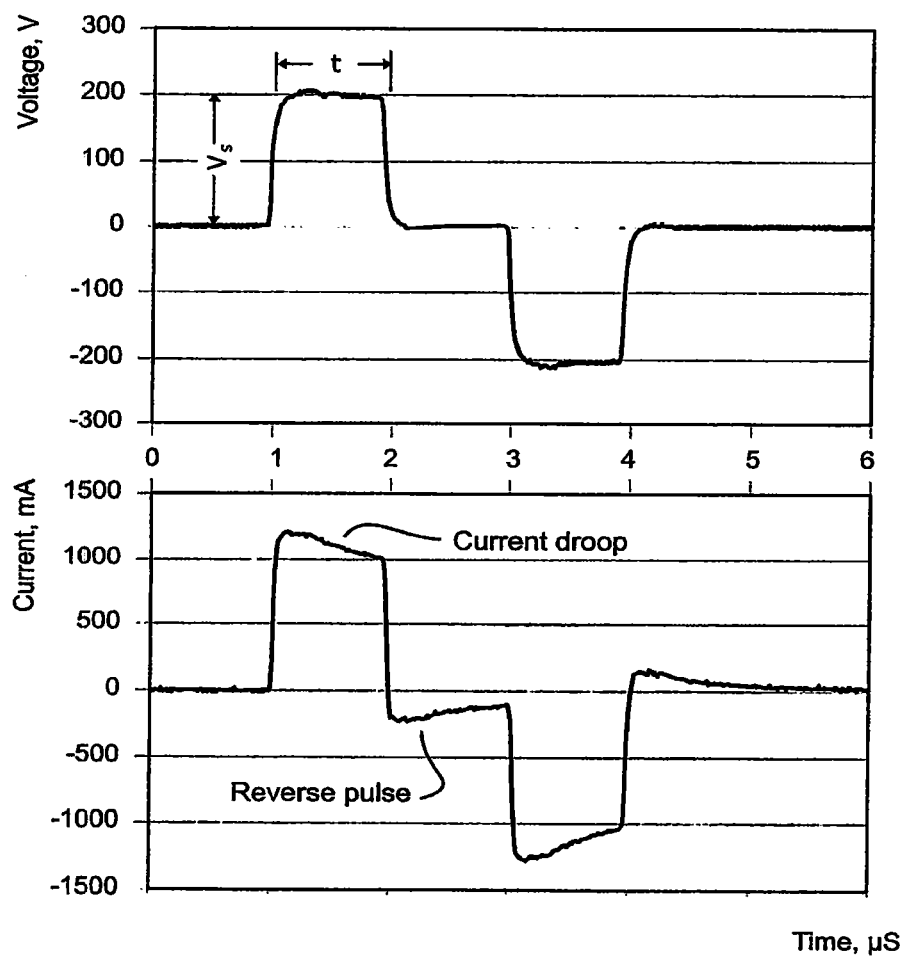
FIG. 5 shows voltage and current of a waveform which is an embodiment of the invention, over a cycle.
Figure 6:
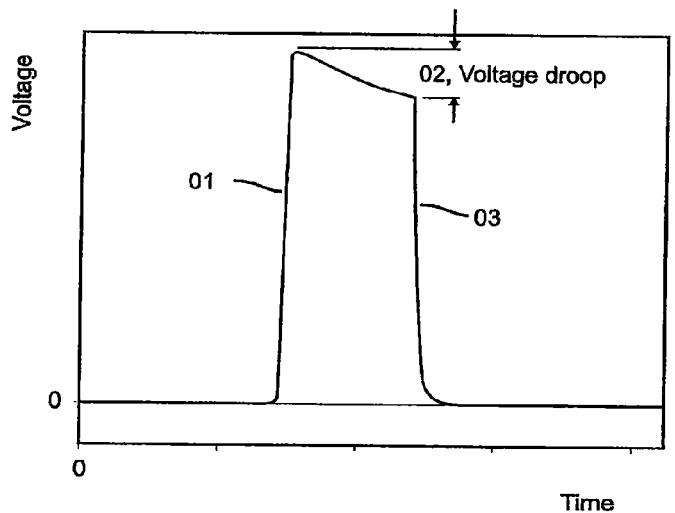
FIG. 6 illustrates a pulse shape according to certain embodiments of the invention, showing an exaggeration of the voltage droop.

The effect of the C and R terms can be seen if one examines the current and voltage in a typical HPSP cycle of pulse time 1 µS and the inter-pulse spacing 1 µS, as shown in FIG. 5. The current trace shows the current falling off during the pulse on-time due to the effect of the series capacitance. During the inter pulse space, the apparatus shorts the electrodes together allowing the capacitance to discharge, which gives rise to the small reverse pulse in the inter pulse space of the same magnitude as the slope on the top of the waveform.

As previously mentioned, for HPSP pulses of short duration with dominant harmonics in the 20 kHz to 2 MHz region, the tissues can be approximated by a resistive load. Consequently, the power dissipation in the load can be estimated by considering only the amplitude of the pulse. The mean power dissipation, $W_m$, can be therefore be approximated to: $W_m=\delta \cdot V_p^2/R$. Where, $V_p$ is the voltage of the pulse and R the measured load resistance and $\delta$ is the duty cycle. This neglects droop on the output current due to the capacitance of the tissues, which means that the power formula is an over estimate for longer pulses.

A better approximation, that can be easily calculated, is given by allowing for the series capacitance in the load equivalent circuit and assuming the cycle time to be long relative to the load time constant, approximating a pulse cycle to the sum of four step inputs as represented by the following expression:

$$\frac{V^2}{R} \cdot \frac{1}{T} \cdot \left[ \int_0^{t_1} e^{-2 \cdot \frac{t}{\tau}} dt + \int_{t_1}^{t_2} \left[ e^{\frac{-t}{\tau}} - e^{\frac{-(t-t_1)}{\tau}} \right]^2 dt + \right.$$
$$\int_{t_2}^{t_3} \left[ e^{\frac{-t}{\tau}} - e^{\frac{-(t-t_1)}{\tau}} - e^{\frac{-(t-t_2)}{\tau}} \right]^2 dt +$$
$$\left. \int_{t_3}^{T} \left[ e^{\frac{-t}{\tau}} - e^{\frac{-(t-t_1)}{\tau}} - e^{\frac{-(t-t_2)}{\tau}} + e^{\frac{-(t-t_3)}{\tau}} \right]^2 dt \right]$$

Where V is the applied voltage, R is the load resistance, $\tau = C \cdot R$ where C is the series capacitance, $t_1 = t_2 = t_3 = t$ is the pulse width and inter-pulse space which are assumed the same and T=the cycle time.

Figure 7:
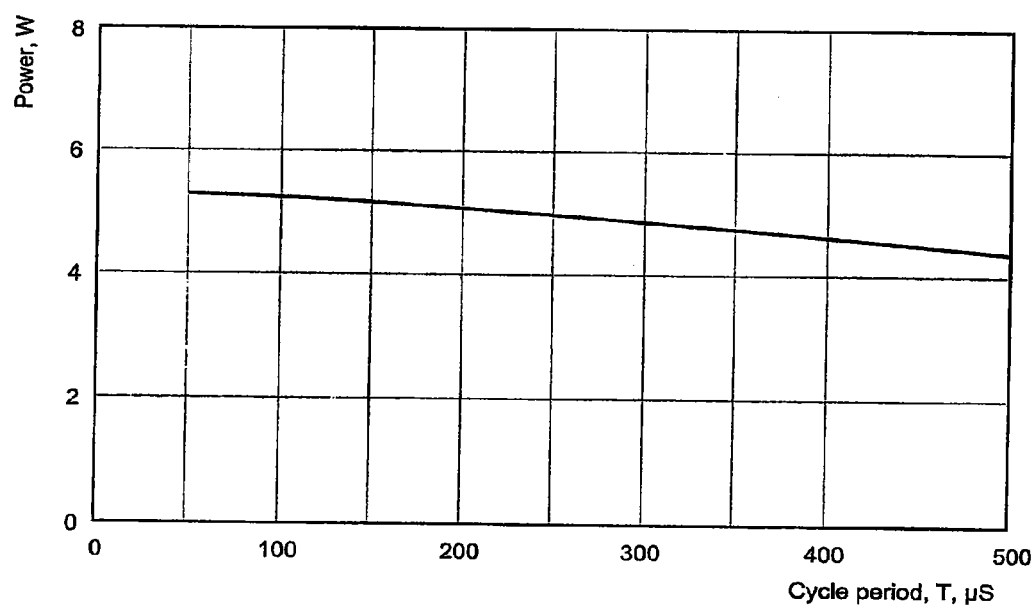
FIG. 7 shows the power dissipated assuming pulse width is varied linearly with cycle frequency, allowing for the droop in the current due to series load capacitance.

The result of this approximation is shown in FIG. 7 where the pulse width is reduced linearly as frequency is increased in an attempt to keep power dissipation constant, according the to ratio: Pulse Width=T/100.

Over the range T=50 to 500 µS this simulates pulse widths varied linearly from 0.5 to 5 µS as the cycle frequency changes from 20 to 2 kHz, with V=200 V, R=150Ω and C=50 nF. For these short pulses, the power dissipation increases from 4.4 to 5.3 W over the range, a difference of 20%. This error may be accounted for by approximating a correction factor to a straight line if required in a practical apparatus, but normally it is acceptable to neglect it as postulated in the preceding paragraph.

At high power levels the tissues start to become warm under the electrodes, which puts a limit on the amount of power that can be delivered to the patient. The typical limitation on tissue heating (with 50×50 mm electrodes, but extendable using larger electrodes) found experimentally is in the range 8-12 W.

Neglecting the droop in current due to series capacitance of the tissues as discussed above, the heating limit may be approximated to: $V_p = \sqrt{(Z \cdot P/\delta)}$, where $V_p$=pulse voltage (V), Z=patient impedance (Ω) which is assumed constant at 150Ω, P is a power limit derived experimentally and $\delta$ is the duty cycle. $\delta = Pw \cdot F_p$, where Pw is the pulse width and $F_p$=number of pulses per second (counting both forward and reverse pulses).

Macdonald and Coates GB2290033 state that heating is a limitation that means that as frequency is increased the voltage has to be reduced; Macdonald quotes 150 V as being the limiting voltage with a mono polar wave at 5 kHz and 25V at 150 kHz. Fitting a curve of constant power through these points gives a power limit which approximates to $V_p = \sqrt{(168/\delta)}$. The power limit assuming a patient impedance of 150Ω as defined above is 1.125 W. At the frequencies specified by Macdonald and Coates, the apparatus according to aspects of this invention has limits of better than 400V and 73V respectively, well over twice those quoted in GB2290033.

Waveform Harmonics

Figure 1:
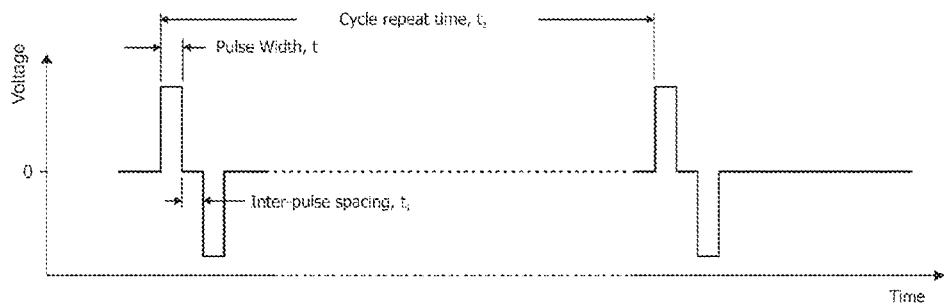
FIG. 1 illustrates a basic continuous bi-phasic wave form, with a large mark space ratio (time axis not shown to scale).
Figure 2:
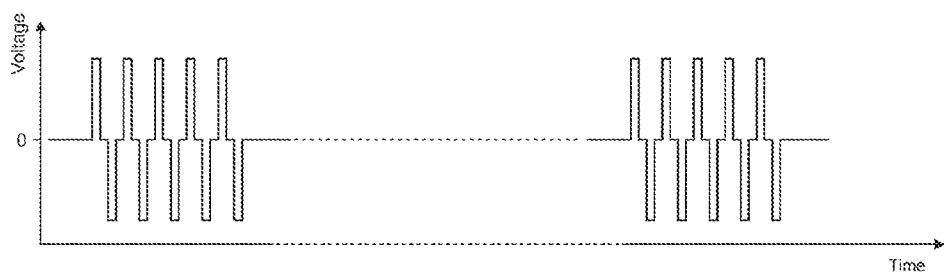
FIG. 2 illustrates a burst waveform having multiple biphasic cycles separated by quiet periods.

An idealised pulse shape for the therapeutic waveform is illustrated in FIG. 1. The pulse train may be either a continuous stream of pulses with a small mark-space ratio, as illustrated in FIG. 1, or in bursts of multiple pulses followed by a gap during which there is no activity, as illustrated in FIG. 2.

Figure 8:
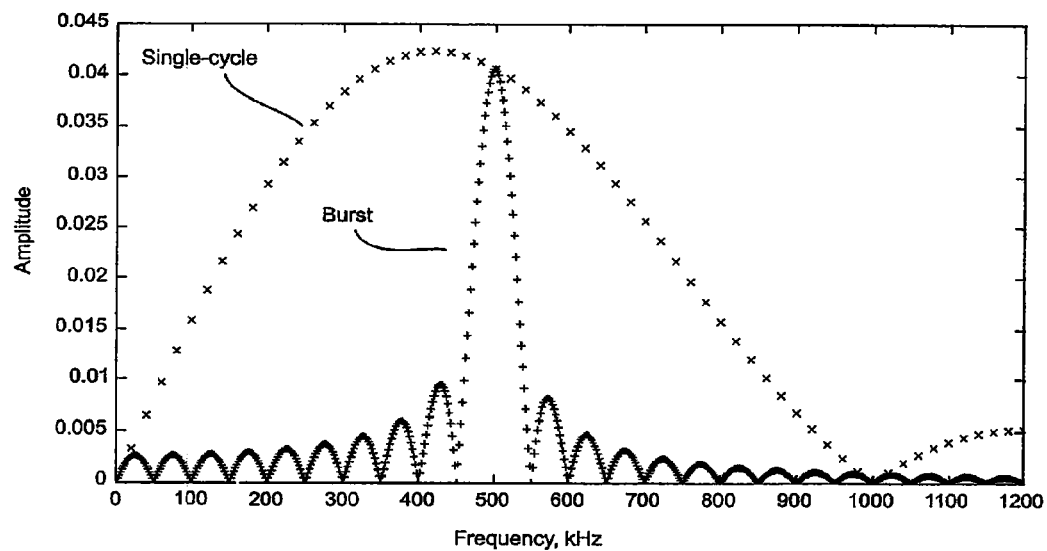
FIG. 8 shows a comparison of continuous and burst waveforms, in the frequency domain.

The frequency content of a waveform is commonly expressed in terms of its components by means of Fourier analysis. FIG. 8 shows the components of two simplified waveforms, similar to FIGS. 1 and 2 but with zero inter pulse space. The single cycle curve represents one cycle of a 500 kHz square wave repeated at 20 kHz. The burst curve is a 500 kHz square wave in bursts of ten cycles repeated at 2 kHz. Consequently the energy of both waveforms is identical. The curves are representative of a biphasic pulse of 1 µS pulse width with zero inter pulse space.

It can be seen from the figure that the single-cycle wave has a series of harmonics at frequencies spaced by 20 kHz spread widely over the spectrum, while the burst wave has harmonics spaced at 2 kHz (i.e. the burst repetition frequency) and has most energy concentrated around a narrow peak at 500 kHz, with little energy outside the range 400 kHz to 600 kHz. This peak becomes more pronounced as the number of cycles in the burst is increased. The single-cycle form may be preferred in certain aspects and embodiments of this invention because it maximizes the possibility of cellular coupling by distributing the energy in the waveform across the spectrum.

Figure 9:
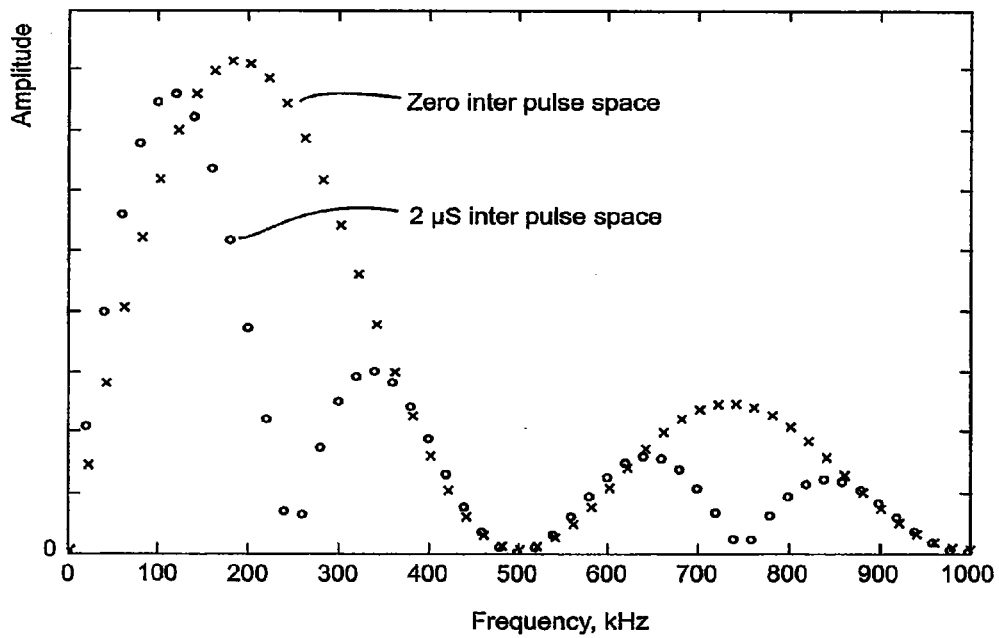
FIG. 9 shows a comparison between a waveform having an interpulse space of 0p and an interpulse space of 2 µs, in the frequency domain.

FIG. 9 shows the components of a square wave of 2 µS pulse width with equal positive and negative pulses and zero inter pulse space, compared with a square wave of the same pulse width with 2 µS inter pulse space, both at a cycle frequency of 20 kHz. The graph shows the familiar spacing between components of 20 kHz, but the waveform with 2 µS inter pulse space has its peak at approximately half the frequency of the waveform with zero space. This can be explained by the fact that the second square wave is representative of the peaks of a sine wave of similar period.

Figure 10:
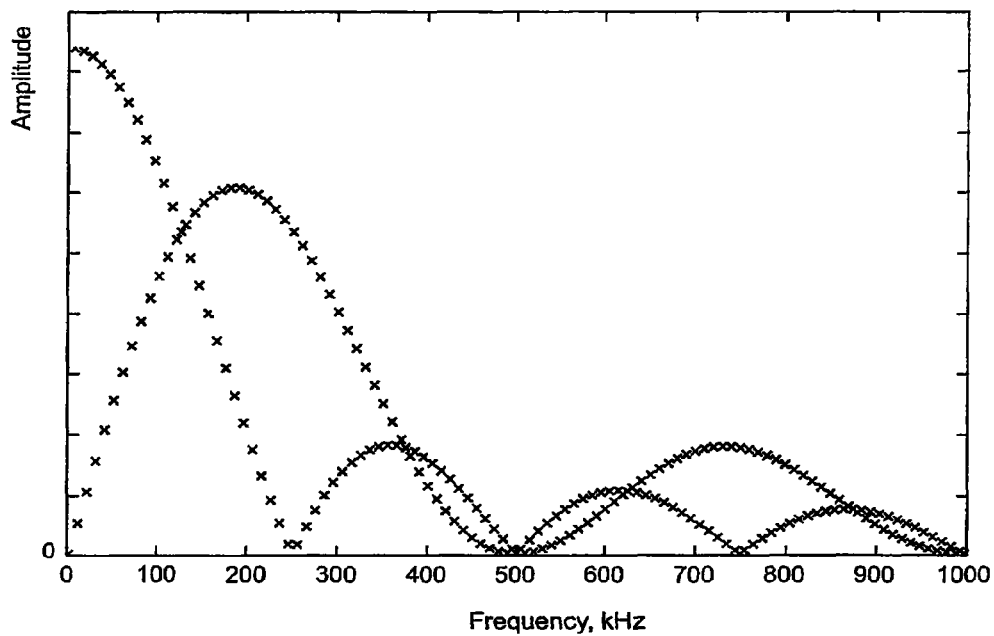
FIG. 10 shows the harmonic components of a 5 kHz, 2 µs biphasic pulse, with a 100 µs interpulse spacing.

FIG. 10 shows a square wave of 2 µS pulse width with cycle frequency of 5 kHz and inter pulse spacing of 100 µS; in this case the return pulses are equally spaced between the forward pulses. This provides an interesting result with two distinct curves made up of harmonic components of the signal. One could be said to represent the harmonic components of the cycle frequency and the other the components of the pulses themselves.

Threshold of Sensation

According to the mechanisms of action postulated, there are two independent modes of action, one related to the generation of action potentials to provide a therapeutic effect as in a TENS machine, and one independent of this based on oscillating electric fields. A gentle tingling sensation is often reassuring for the patient and as previously mentioned this may also play an important role in the expression of neurotransmitters.

Table 1 shows threshold of sensation as a function of pulse width and pulse amplitude using HPSP stimulation. Electrodes were placed on the forearm over the median nerve, spaced 170 mm apart, with the leading pulse nearest to the elbow. The waveform used was a symmetrical biphasic waveform with a fixed 1 µS inter-pulse space as illustrated in FIG. 5. The pulse width, t, was varied as specified in Table 1. The pulse amplitude is the minimum voltage, $V_s$, zero to peak recorded across the electrodes that produces sensation. In the biphasic waveform used the peak to peak voltage value is twice that expressed in Table 1.

TABLE 1

Voltages required to produce sensation at various pulse widths and frequencies employing a symmetrical biphasic waveform as shown in FIG. 5 with a fixed 1 μS inter-pulse space.

| Pulse Width, μS | Voltage (zero to peak) at threshold of sensation at various cycle repetition frequencies | | | |
|---|---|---|---|---|
| | 5000 Hz | 2500 Hz | 1000 Hz | 100 Hz |
| 1.5 | 189 | 185 | 171 | 188 |
| 2 | 146 | 136 | 127 | 132 |
| 3 | 84 | 80 | 79 | 78 |
| 4 | 63 | 60 | 59 | 57 |
| 5 | 48 | 49 | 50 | 48 |
| 6 | 39 | 40 | 38 | 38 |
| 8 | 28 | 29 | 29 | 29 |
| 10 | 23 | 25 | 23 | 25 |
| 20 | 12 | 12 | 12 | 13 |

Figure 11:
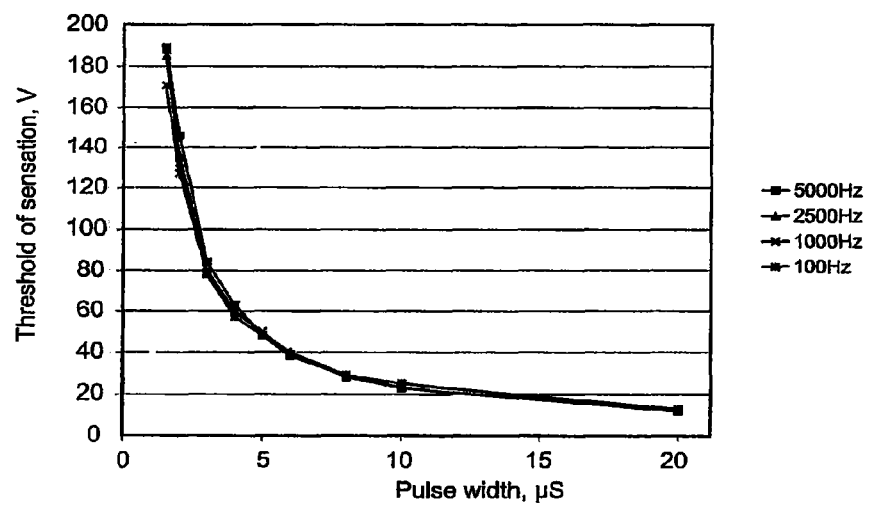
FIG. 11 shows the relationship between the threshold of sensation and voltage at different pulse widths for four cycle frequencies with a fixed interpulse spacing of 1 µs.
Figure 12:
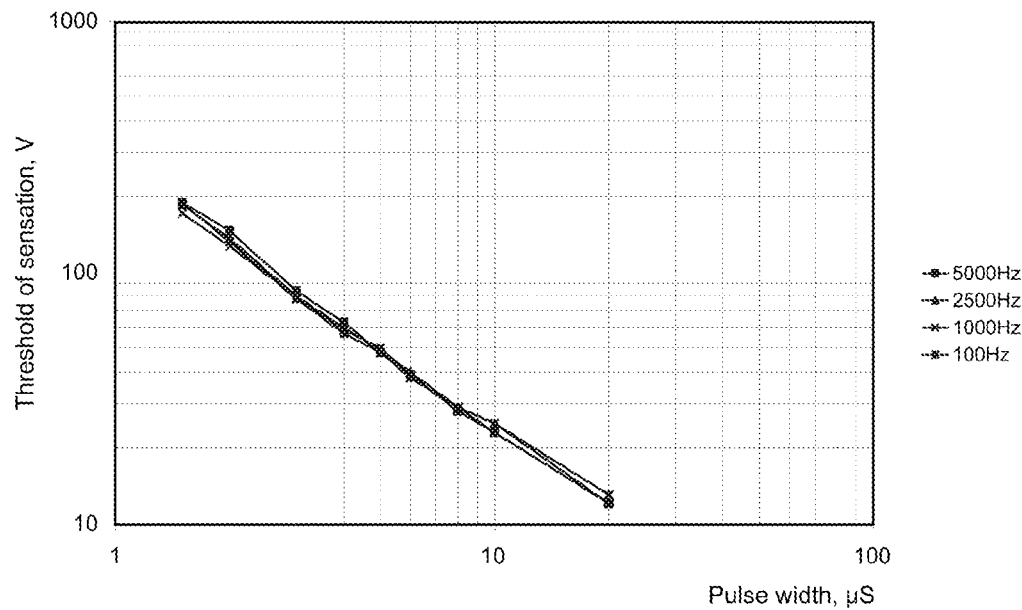
FIG. 12 shows the relationship between the threshold of sensation and voltage at different pulse widths for four cycle frequencies, on a log-log scale.

The results in Table 1 are illustrated graphically in FIG. 11. This curve is a straight line when plotted on a log-log scale as shown in FIG. 12. By inspection of this curve, the relationship between the minimum voltage, $V_s$, that produces sensation and pulse width, p, for a fixed 1 μS inter pulse space, may be approximated by the following relationship: $V_s = k\, p^m$, where k and m are constants and for this case k=270 and m=−1.0265.

Although derived quite differently, the curve in FIG. 11 looks remarkably similar in shape to the 'strength-duration curves' observed by Li et al 1976. Here they studied the amplitude required, for any given duration of a single pulse applied to a dissected nerve, to produce an action potential recorded from that nerve. Their observations and the generally accepted view today, is that the strength duration curve indicates that the stimulus current and duration can be mutually traded off over a certain range.

However, this view is not consistent with our results. Table 1 and FIGS. 7 and 8 reveal the effects of the minimum amplitudes required to produce sensation from 50×50 mm surface electrodes placed on the forearm at a variety of pulse durations from 0.5 to 20 μS: at each given pulse duration, the effects of four different cycle frequencies (ranging from 100 Hz to 5 kHz) were compared when we employed the type of short high power pulses that we can now generate. It can be seen that sensation occurs at stimulation rates well above the accepted physiological limits, and also that at each pulse duration the threshold of sensation does not vary greatly with cycle frequency, despite the fact that the amount of current at any given amplitude that flows over a period of time is directly proportional to cycle frequency. The mean modulus current (proportional to rate of charge transferred) flowing in the patient at 5 kHz is 50 times that at 100 Hz, but from this observation at any given pulse duration the threshold of sensation is almost the same. For example, with a pulse of 2 μS duration, the experimentally measured mean modulus current at 100 Hz was 0.27 mA (approx 15 mA RMS), whereas at 5,000 Hz it was 13.5 mA (approx 95 mA RMS). With a typical TENS pulse of 50 μS or more, the former would represent a painful level of stimulation and the latter an intolerable one.

We next investigated the effect of varying inter pulse spacing. The data reported below was also obtained with electrodes over the median nerve as described previously. Table 2 shows the relationship between threshold of sensation and inter pulse spacing for a 5 kHz cycle frequency, 1.5 μS biphasic pulse.

TABLE 2

Voltages required to produce sensation at various pulse inter pulse spacing at 5,000 Hz cycle frequency employing a symmetrical biphasic waveform of 1.5 μS pulse width.

| Inter pulse space, μS | Onset of sensation, V |
|---|---|
| 0.5 | 222 |
| 1 | 202 |
| 1.5 | 162 |
| 2 | 150 |
| 3 | 124 |
| 4 | 114 |
| 5 | 100 |
| 6 | 94 |
| 8 | 90 |
| 10 | 86 |
| 20 | 83 |
| 50 | 79 |
| 100 | 76 |

Figure 13:
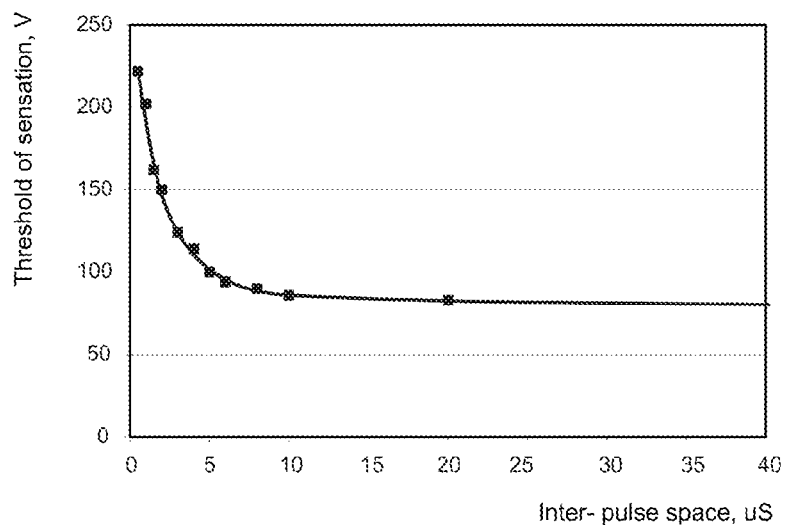
FIG. 13 shows the voltages required to produce sensation at various interpulse spacings at a 5,000 Hz cycle frequency, employing a symmetrical biphasic waveform of 1.5 µs pulse width.

These results are presented graphically in FIG. 13. It can be seen that there is a rapid reduction in the voltage at which first sensation is felt as inter pulse spacing is increased from 0.5 to approximately 10 μS, after which sensation is virtually independent of inter pulse spacing.

If one considers a 2,500 Hz HPSP waveform of 0 μS inter pulse space, compared with an identical one of 1 μS inter pulse space, the threshold of sensation is 200V compared to 140V for 2 μS pulse width, but only 50V compared to 48V for 5 μS pulse width. With pulses of the order of 2 to 4 μS and voltages of the order of 200V, it is possible to vary the level of sensation between an intense tingling and little or no sensation by varying only the inter pulse spacing between 0 and 10 μS. This provides a new approach to controlling the perceived level of treatment in an electrotherapy apparatus, while delivering a constant treatment current to the patient. It also represents a new way of modulation of the sensory nerves at rates within the physiological range for signals that are delivered at high continuous power levels so as to penetrate deep tissues. This may be also combined with control of the overall amplitude of the signal.

The threshold of sensation reported here is the minimum level of stimulation at which the subject reports the first sensation. After a few seconds, the nerves habituate and this sensation disappears. A typical level of stimulation employed would be somewhat higher even for very mild sensation. These sensation limits therefore provide useful benchmark at which the minimum level of treatment may be set, thereby delivering maximum charge to the patent for a given waveform without discomfort. It should be noted that the level of sensation varies a little on other parts of the body, for instance it is slightly higher with electrodes on the spine over T1 and T12.

These results demonstrate that it is possible to independently control the edge rate and amount of charge that can be delivered safely and comfortably to the patient, and the level of sensation that the patient feels, by variation of cycle frequency, inter pulse space and pulse width. The ability to deliver high average currents at high voltages interpedently of sensation levels allows those modes of action based on electric field effects to be maximised and penetration of large volumes of deep tissues to be achieved.

Medical Observations

In certain aspects and embodiments, this invention allows pulses to be applied that can affect function within deep tissues in the periphery or centrally without distress, while producing beneficial changes particularly within inflamed regions.

When applied to painful musculoskeletal regions, whether associated with acute or chronic conditions, a temporary reduction in tenderness and suffering tends to be produced within 60 mins. There have been no reported side effects and no limitations have been found for long term stimulation.

To give an example of the surprising amount of tissue that can be treated without producing sensation: one 50×50 mm surface electrode can be placed on the sole of one foot and the other on the other foot, allowing signals to traverse one leg to the other. In this manner aches and pains in any region (e.g. knee or hip) in both lower limbs can be relieved simultaneously.

The parameters used for the study were biphasic waveforms of 0.5 μS pulse width at 20 kHz cycle frequency with a interpulse space that varied from 0-4 μS at mean pulse voltages of typically 220V.

Table 3 gives details of a pilot study where electrodes were placed in 17 patients suffering acute and chronic musculoskeletal pain while being treated with HPSP at 20 kHz for 60 mins. All had 50% or more relief of pain immediately after treatment was discontinued.

TABLE 3

| No | Sex | Age | Duration of pain (mth) | Site of tenderness and associated cause (Key: č = associated with) | Sites of electrode of one polarity | Sites of electrodes of the other polarity (Key: if two or more electrodes are attached to this polarity they are differentiated by FIGS. 1, 2,3 etc) |
|----|-----|-----|------------------------|--------------------------------------------------------------------|------------------------------------|------------------------------------------------------------------------------------------------------------------------------------------------------|
| 1 | F | 48 | 240 | Both legs from knee to ankle following road traffic accident | Mid-line of back at the level of L4 | 1: dorsum of right foot<br>2: dorsum of left foot |
| 2 | M | 43 | 12 | Right neck and arm pain č ankylosing spondylitis | Palm of right hand | Back of neck, at the level of C5 |
| 3 | F | 26 | 0.10 | Region overlying fractured cuboid bone of left foot | Dorsum of left foot | 1: origin of the long extensors of the left foot<br>2: origin of the long flexors of the left foot |
| 4 | F | 53 | 0.16 | Left scapula pain associated with č cervical spondylosis | Front of neck at the level of C5 | 1: back of neck at the level of C3<br>2: back of neck at the level of C7 |
| 5 | M | 75 | 3 | Right shoulder and upper arm pain | Anterior aspect of the right elbow | 1: in the shoulder region over acromioclavicular joint<br>2: in the upper chest region overlying pectoralis major |
| 6 | F | 48 | 168 | Back pain č tender erector spinae and abdominal oblique muscles on both sides from T12 downwards | Mid-line of the back at the level of T12 | 1: over the left anterior superior iliac spine<br>2: over the right anterior superior iliac spine |
| 7 | F | 42 | 4 | Post-operative pain in the left hypogastric and inguinal region č hysterectomy | On the abdomen just above the tender region | 1: on the abdomen just below the tender region to the left side of it<br>2: on the abdomen just below the tender region to the right side of it |
| 8 | F | 74 | 60 | Pain in cervical region and vertigo č cervical spondylosis | On the mid-line of the back of the neck at the level of C2 | 1: on the palm of the left hand<br>2: on the palm of the right hand |
| 9 | M | 42 | 48 | a tender neck and jaw region on the right side č migrainous neuralgia | Right cheek | Right side of the neck overlying the supraclavicular region |
| 10 | F | 38 | 192 | Back pain č herniation of L5/S1 intervertebral disc | Mid-line of the back at the level of L5/S1 | 1: on the anterior aspect of the abdomen at the level of L5/S1 a hand's breadth to the left of the mid line<br>2: on the anterior aspect of the abdomen at the level of L5/S1 a hand's breadth to the left of the mid line |
| 11 | M | 52 | 0.4 | Pain and incapacity č a tender right loin and degenerative changes and osteophyte formation at the level of L5/S1 | Mid-line of the back at the level of T12 | right inguinal region |
| 12 | M | 66 | 1.35 | Pain in the right sacro-iliac region | Right buttock overlying gluteal region | 1: on the back overlying the iliolumbar ligament<br>2: on the back just above the iliac crest a hand's breadth to the right of B[1] |
| 13 | M | 63 | 2 | Pain in the right thumb č swollen, tender first metacarpophalangeal joint | At the base of the neck overlying the right supraclavicular fossa | over the anterior aspect of the right thumb |
| 14 | F | 36 | 36 | Left shoulder pain | On the left side of the neck over transverse process of C3 | 1: on the back overlying left middle trapezius<br>2: on the back overlying left serratus anterior |
| 15 | M | 60 | 1 | Right buttock and thigh pain č tender quadratus lumborum muscle | In the mid-line of the back at the level of T12 | 1: on the back overlying 2: sacro-iliac joint overlying the right loin |

TABLE 3-continued

| No | Sex | Age | Duration of pain (mth) | Site of tenderness and associated cause (Key: č = associated with) | Sites of electrode of one polarity | Sites of electrodes of the other polarity (Key: if two or more electrodes are attached to this polarity they are differentiated by FIGS. 1, 2,3 etc) |
|---|---|---|---|---|---|---|
| 16 | M | 67 | 18 | Low back pain | In the mid-line of the back at the level of L5 | 1: on the buttock overlying the right gluteal region<br>2: on the buttock overlying the right gluteal region |
| 17 | M | 77 | 5 | Tender ankle č paratendinitis of Achilles tendon | Sole of foot | 1: above the tender region to the left<br>2: above tender region to the right |

Detailed Description of an Electrotherapy Apparatus

Figure 14:
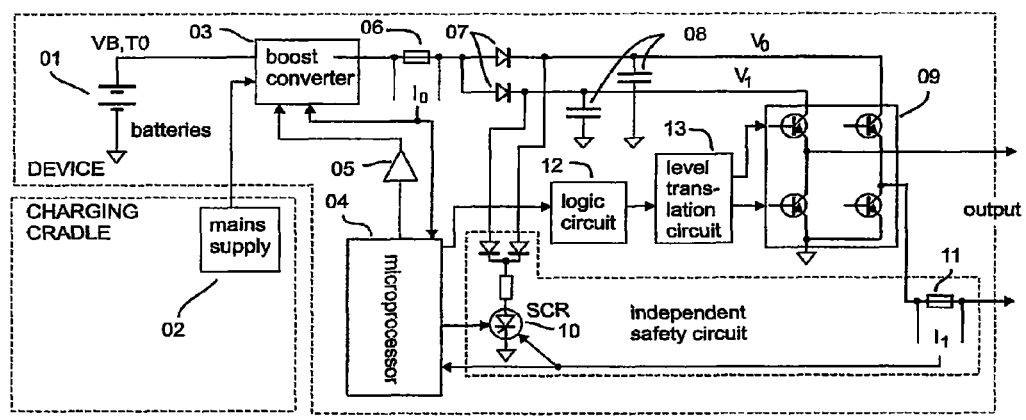
FIG. 14 shows a block diagram of an embodiment of the apparatus according to one aspect of the invention.

With reference to FIG. 14, the apparatus comprises a boost converter, 03, which produces a variable high voltage typically in the range of 0-500V from either the batteries, 01, or from an external mains power supply, 02.

The level of the output voltage is commanded by a microprocessor, 04, via a digital to analogue converter or other means, 05. The output current of the power supply is sensed by a circuit, 06, and the measured current, $I_O$, is fed back into hardware circuitry in the boost converter to provide either a current limit or current control loop and also fed into the microprocessor for monitoring purposes. The boost converter is designed such that the maximum voltage and current that it can produce continuously is limited to a safe maximum in hardware and the microprocessor only sets the output within these limits.

The output stage of the device consists of an H-bridge arrangement, 09, that allows the forward and reverse pulses of the output waveform to be synthesized by switching sequences generated by the logic circuit, 12, under control of the microprocessor. The logic circuit includes a circuit which limits the pulse width independently of the microprocessor; this is important for limiting the charge delivered to the patient under fault conditions as discussed later.

Level translation circuitry, 13, is also provided. This is the electronics that translates the logic level signals from the logic circuit, 12, to signals referenced to the high voltage DC supply to provide switching signals for the output transistors. This level translation circuit is designed such that the output transistors cannot remain in the on state for longer than a fixed period (typically 200 μS). This provides two levels of protection. Firstly it limits the maximum period that a pulse can be applied to the patient in normal operation which acts as a back-up to the pulse width limiting function implemented in the logic block and described in the previous paragraph. Secondly, it provides a further level of protection against microprocessor failure, since the microprocessor may be expected to fail with its outputs in a frozen state (additional protection against microprocessor failure is provided by a watchdog circuit that is periodically reset by the system, not shown on the figure).

The two arms of the H-bridge, 09, are fed by two bus capacitors, 08, through two diodes, 07. Each bus capacitor is sized identically and provides the energy for the forward and reverse pulses respectively. The typical shape of a single forward or reverse pulse is illustrated in FIG. 10 with the slope of the top of the pulse exaggerated for clarity. The waveform exhibits high rates of a change on its forward and trailing edges, and is substantially of square wave form except for the droop in the bus, 02, which is the result of partial discharge of the bus capacitor supplying the energy for the pulse. It should be noted that the trailing edge, 03, has a rapid descent to zero volts. This is achieved by turning on both bottom devices in the H-bridge arrangement during the off period.

As previously discussed, limitation of charge delivered to the patient is a key consideration in the safety of the apparatus, it should not exceed the limit of 75 μC which is the value at which charge may be hazardous through the chest (AAMI NS4) and it should also not exceed 300 mJ per pulse (IEC 60601-2-10). The bus capacitors are designed such that the total charge delivered to the patient can never reach dangerous levels even in the event of multiple component failure causing the entire stored charge to be delivered. The charge delivered to the patient is calculated by adding the charge transferred in positive and negative cycles and the continuous output of the boost converter during the pulse time. For this reason, the boost converter cannot be sized to maintain the voltage on load during the pulse output. The arrangement of separate forward and reverse bus capacitors permits the forward and reverse pulses to deliver essentially identical charge to the patient despite the droop in the bus, thereby ensuring that there is no net DC current which prevents adverse reactions caused by ionic transport to one or more electrodes. With HPSP waveforms, pulse currents of 1-4 A maximum are preferred (higher pulse currents may be possible).

Here, the output stage uses two ceramic type capacitors, each providing the forward and reverse pulses so that a balanced, approximately square wave biphasic pulse of the type shown in FIG. 5 is produced.

Referring back to FIG. 14, as secondary protection an independent safety circuit is provided. This consists of an output current sensor, 11, and Silicon Controlled Rectifier (SCR), 10, and other sensing and reference circuitry not shown in the figure that independently measures the bus voltage and the current applied to the patient. The circuit provides two main functions:

a) it discharges both buses in the event that either the bus voltages $V_0$ and/or $V_1$ or the output current $I_1$ exceeds limits set by the standards.

b) it provides a second means of measuring the currents and voltages generated by the primary circuit which are reported to the microprocessor.

The SCR can also be operated externally by the microprocessor, thereby providing a means of discharging the DC buses in the event of shutdown or an error identified by the microprocessor. The output current sensor is shown in the output circuit in the figure.

The independent circuit allows the microprocessor to determine if there is a failure in the voltage control part of the boost converter, by comparing the voltage set point with the voltage reported by the independent circuit. In addition the system voltage reference is continually checked by the microprocessor against a further secondary reference. Further the microprocessor makes another safety check by comparing the average output current of the boost converter with the average patient current.

Consequently, the apparatus comprises three sub-systems:
a) The power supply and output stage which is the means of generating and controlling the output waveform and also has limits for output parameters such as voltage and current implemented in hardware and a means of reporting the values of key parameters.
b) The independent safety circuit which provides a secondary means of limiting the output parameters to safe values, and reporting measured values.
c) A means of controlling the output level by reducing the output of the first circuit from its maximum safe value and a means of comparing the voltages and currents sensed by the two independent circuits, thereby identifying if there is an error in either circuit and causing shut-down of the device.

REFERENCES

Duggan A W, Foong F W (1985) Biciculline and spinal inhibition produced by dorsal column stimulation in the cat. *Pain* 22:249-259
Johnson M I, Ashton C H, Thompson J W (1991) An in-depth study of long-term users of transcutaneous electrical stimulation (TENS). Implications for clinical use of TENS. *Pain* 44:221-229
Kotnik T, Miklavčič D (2000) Second-order Model of Membrane Electrical Field Induced by Alternating External Electrical Fields. *IEEE Transactions on Biomedical Engineering* 47:1074-1081
Li C L, Bak A (1976) Excitability of the A- and C-fibers in a peripheral nerve. *Experimental Neurology* 50:67-79
Liu D-S, Astumian R D, Tsong T Y (1990) Activation of Na+ and K+ pumping modes of (Na,K)-ATPase by an oscillating electric field. *The Journal of Biological Biochemistry* 265:7260-7267.
Macdonald A J R, Coates T W (1995) The discovery of transcutaneous spinal electroanalgesia and its relief of chronic pain. *Physiotherapy* 81:653-661
Melzack R, Wall P D (1965) Pain Mechanisms: a new theory. *Science* 150:971-979.
Salar G, Job I, Mingrino S, Bosio A, Trabucchi M (1981) Effect of transcutaneous electrotherapy on CSF β-endorphin content in patients without pain problems. *Pain* 10:169-172
Stinus L, Auriacombe M, Tignol J, Limoge A, Le Moal M (1990) Transcranial electrical stimulation with high frequency intermittent current (Limoge's) potentiates opiate-induced analgesia: blind studies. *Pain* 42:351-363
Towell A D, Williams D, Boyd S G (1997) High frequency non-invasive stimulation over the spine: effects on mood and mechanical pain tolerance in normal subjects. *Behavioural Neurology* 10: 61-65
Wall P D (1986) The discovery of Transcutaneous Electrical Nerve Stimulation. Journal of Orthopaedic Medicine 3: 26-28.
Woolf C J (1989) Segmental afferent fibre-induced analgesia: transcutaneous electrical nerve stimulation (TENS) and vibration. In: The Textbook of Pain. Eds: Wall, P. D., Melzack R. $2^{nd}$ Ed. Churchill Livingston, pp 884-896.

What is claimed is:

1. An apparatus for producing analgesia in a patient through electrical signals applied by electrodes to the patient's body, the apparatus comprising electrodes for application to the patient's body and a signal generator which is connectable to the electrodes, wherein the signal generator is arranged to generate a biphasic waveform comprising successive cycles each containing a positive and negative pulse, and comprises:
  a converter for producing a desired voltage from a power supply;
  a first capacitor which is in electrical connection with said converter and which is arranged to provide the positive pulse to one of said electrodes;
  a second capacitor which is in electrical connection with said converter and which is arranged to provide the negative pulse to one of said electrodes;
  wherein said first and second capacitors are respectively connected to an output by a corresponding first and second pathway, the pathways including respective switches, and wherein the signal generator includes a controller arranged to control the operation of the switches to cause alternate discharge of the first capacitor through the corresponding first pathway and the second capacitor through the corresponding second pathway to generate said positive and negative pulses, and wherein the first and second capacitors are connected via respective diodes to a common supply generated by the converter, and wherein the first and second pathways are provided respectively by two arms of an H-bridge.

2. The apparatus of claim 1, wherein the capacitance of the capacitor decreases with voltage.

3. The apparatus of claim 1 wherein the capacitors are ceramic type capacitors.

4. The apparatus of claim 1, wherein the output has a peak pulse selected from a current of greater than 1 A and a current of greater than 2 A.

5. The apparatus of claim 1, wherein the apparatus comprises a control to control the operation of switches, such that during the pulse off time, the switches in the pathway connecting the first and second capacitor to the respective output are switched off, and one or more additional switches are operated to short the patient outputs.

6. The apparatus of claim 1, wherein the signal generator is arranged to generate a biphasic waveform wherein each pulse of the biphasic waveform has an edge rate selected from an edge rate greater than 250 V/µs and an edge rate greater than 500 V/µs.

7. The apparatus according to claim 1, wherein the apparatus further comprises means to limit the pulse width to less than a predetermined period.

8. The apparatus of claim 7, wherein the pulse "on" time is limited by circuitry in the switch drive logic or level translation circuitry.

9. The apparatus of claim 7, wherein the pulse length is limited by one or both of a logic circuit and output transistors, which cannot remain in the "on" state for more than a fixed period without edge transitions on the gate drives.

10. The apparatus according to claim 1, wherein the apparatus further comprises means for detecting when said positive or negative pulse is of over-prolonged duration, and for limiting said duration.

11. The apparatus of claim 1, wherein the therapeutic pulse charge does not exceed a safe value in the event of software failure or single component failure.

12. The apparatus of claim 11, wherein said safe value is 75 µC.

13. The apparatus of claim 1, having means for earthing said electrical connection of each of said first and second capacitors, thereby to halt the provision of said pulses.

14. The apparatus of claim 13, wherein said earthing means comprises a switch controlled by said controller.

15. The apparatus of claim 1, wherein the apparatus further comprises one or more independent means for monitoring the signal produced by the apparatus.

16. The apparatus of claim 1 wherein the signal generator is arranged to generate a biphasic waveform comprising successive cycles each containing a positive and negative pulse, wherein the mean pulse width $P_w$ is 10 μs or less, and wherein $V_p^2 \cdot Pw \cdot F_p$ is at least 200, where $V_p$ is the mean pulse voltage, and $F_p$ is the number of forward and reverse pulses per second.

17. The apparatus of claim 16, wherein the mean pulse width is selected from a pulse width of 4 μs or less, 1.5 μs or less, and 0.75 μs or less.

18. The apparatus of claim 16, wherein the mean pulse voltage is selected from at least 100V and at least 150V.

19. The apparatus of claim 16, wherein the voltage is at least 100V and the pulse width is 6 μs or less.

20. The apparatus of claim 16, wherein the voltage is at least 200V and the pulse width is 1.5 μs or less.

21. The apparatus of claim 16, wherein the pulse frequency is selected from at least 1000 Hz and at least 5 KHz.

22. The apparatus of any one of claim 16, wherein the biphasic wave is continuous.

23. The apparatus of claim 16 wherein the signal generator is arranged to provide a biphasic waveform providing a mean modulus current flowing through the patient selected from at least 3 mA, at least 6 mA, and at least 10 mA.

24. The apparatus of claim 16, wherein the interpulse spacing is selected from less than 4 μs, less than 1 μs, and 0 μs.

25. The apparatus of claim 1, wherein $V_p^2 \cdot Pw \cdot F_p$ is selected from at least 250 and at least 340.

26. A method of inducing analgesia in a patient, the method comprising providing an apparatus according to claim 1, applying the electrodes to the patient's body, and providing a waveform as described.

* * * * *